(12) United States Patent
Niklasson et al.

(10) Patent No.: US 7,560,609 B2
(45) Date of Patent: Jul. 14, 2009

(54) DIABETIC MODEL

(76) Inventors: Bo Niklasson, Grevgatan 38, S-114 53 Stockholm (SE); Åke Lernmark, Birger Jarlsgatan 61, S-216 11 Limhamn (SE)

( * ) Notice: Subject to any disclaimer, the term of this patent is extended or adjusted under 35 U.S.C. 154(b) by 291 days.

(21) Appl. No.: 10/487,134

(22) PCT Filed: Aug. 21, 2002

(86) PCT No.: PCT/IB02/03957

§ 371 (c)(1),
(2), (4) Date: Aug. 12, 2004

(87) PCT Pub. No.: WO03/019197

PCT Pub. Date: Mar. 6, 2003

(65) Prior Publication Data

US 2004/0265793 A1   Dec. 30, 2004

(30) Foreign Application Priority Data

Aug. 22, 2001   (GB)   ................................. 0120437.9

(51) Int. Cl.
*A01K 67/00* (2006.01)
*A01K 67/033* (2006.01)

(52) U.S. Cl. .......................................................... 800/9
(58) Field of Classification Search ..................... None
See application file for complete search history.

(56) References Cited

FOREIGN PATENT DOCUMENTS

WO   WO 9811133 A1 *   3/1998

OTHER PUBLICATIONS

Niklasson et al., 1999, Virology, vol. 255: 86-93.*
Schoenecker et al., 2000, Applied Animal Behaviour Science, vol. 68: 349-357.*
Natural Sciences Facility, "Behavioural Biology", pp. 704-705.

* cited by examiner

*Primary Examiner*—G. R Ewoldt
*Assistant Examiner*—Amy E Juedes
(74) *Attorney, Agent, or Firm*—Kohn & Associates PLLC

(57) ABSTRACT

The invention relates to an animal model for diabetes and a method for obtaining said animal model. The invention also relates to the uses of the animal model for screening for or testing compounds for treating or preventing diabetes symptoms. The invention further relates to an assay for determining an individual's susceptibility to developing diabetes. The invention also relates to nucleic acid molecules isolated from Ljungan virus and to polypeptides encoded by any portion of said nucleic acid molecule.

9 Claims, 16 Drawing Sheets

Fig. 1A   Fig. 1C 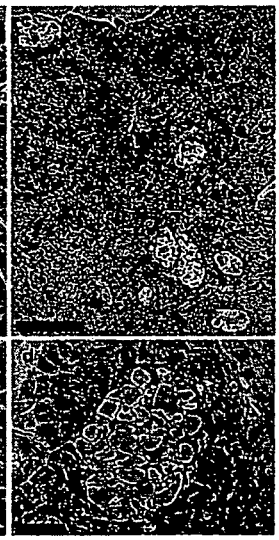  Fig. 1E   Fig. 1G 
      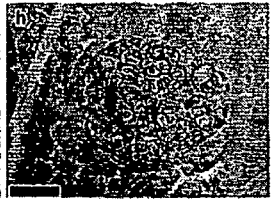
Fig. 1B  Fig. 1D  Fig. 1F  Fig. 1H
Fig. 1

Fig. 3A
Fig. 3B
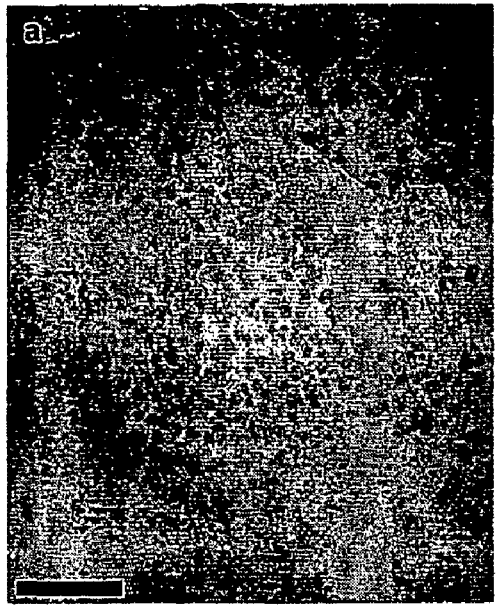
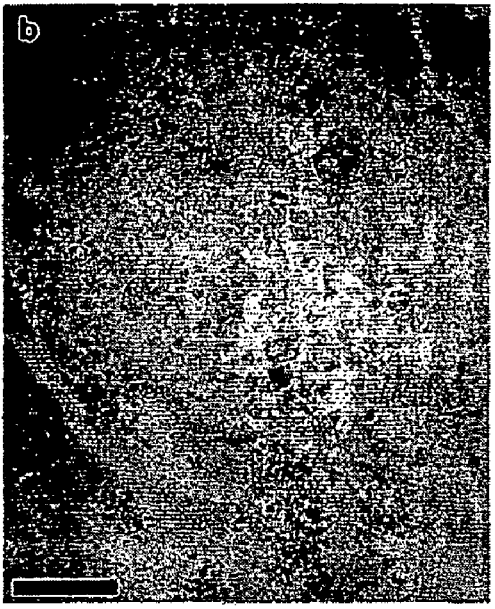
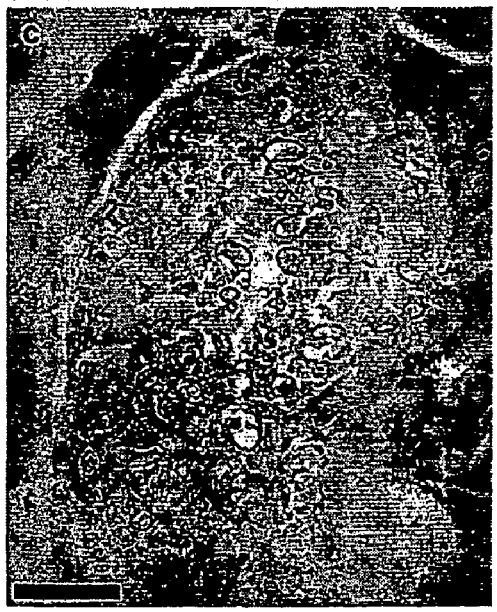
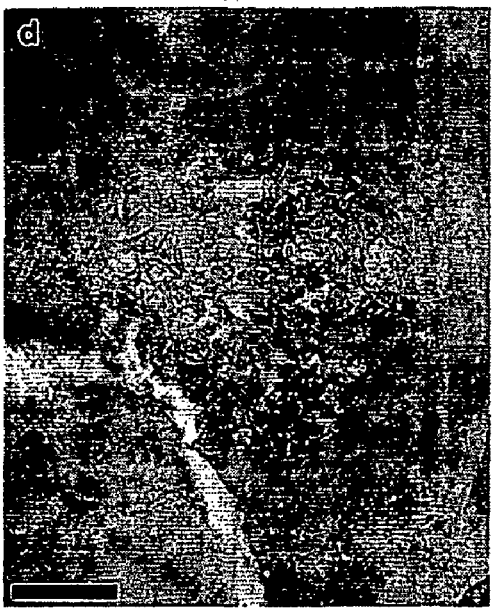
Fig. 3C
Fig. 3D
Fig. 3

Fig. 5 a Ljungan virus molecular mimicry to islet autoantigens.

```
87012   121  DSRYFAAVRCGFHIDVDLNVN IGSAGDLIAAYMPXTAHDHMNTYTFGSYTNLPHVLMHAA 180
GAD65   443        *LD**R*VD*              **VE*D***                        452
IA2     551                                                                  569

87012   721  SFRCPVFFFPLPAPREATSRSILERVDEAVAEELEAVLEARTPDAPLRLKFNPEDPLKDL 780
IA2     964                              *V***VH*I*R*                        976

87012  1081  PMEDNRDEGWREFVDVSMSFRHVEWWLTMFKKVYNVLKSIFAPSIEDKAVDWIDRNDEYI 1140
GAD65   237                                         **S*                     241

87012  1259  TDSEFMDGYIDDIHIIDDAGDNREEKDLALLDDCISSVPFTVPMADLTEKGTFYTSKIV 1318
INS      45                                                 *R*F***P*         53
```

SEQ ID NO. 12
SEQ ID NO. 7
SEQ ID NO. 11
SEQ ID NO. 6
SEQ ID NO. 10
SEQ ID NO. 5
SEQ ID NO. 9
SEQ ID NO. 8
SEQ ID NO. 4

Fig. 7 (SEQ ID NO. 1)

```
TTTGAAAGGGGTCTCCTGGTGGGGTGGGTACACTTCTCGCTCGATGAGTGGGGGTGTGGCTC
ATTGCCCACACCTGGTTGGTTCCCAGGTTCATACAATAACCATCAATAAACTTTTAACATCT
AAGATAGTATTATCCCATACTAGACTGGACGAAGCCGCTTGGAATAAGTCTAGTCTTATCTT
GTATGTGTCCTGCACTGAACTTGTTTCTGTCTCTGGAGTGCTCTACACTTCAGTAGGGGCTG
TACCCGGGCGGTCCCACTCTTCACAGGAATCTGCACAGGTGGCTTTCACCTCTGGACAGTGC
ATTCCACACCCGCTCCACGGTAGAAGATGATGTGTGTCTTTGCTTGTGAAAAGCTTGTGAAA
ATCGTGTGTAGGCGTAGCGGCTACTTGAGTGCCAGCGGATTACCCCTAGTGGTAACACTAGC
CTCTGGGCCCAAAAGGCATGTCATTTGACCACTCAGGTACACAACCCCAGTGATGCACACGC
TTAGTAATGGCTTAGTAACAAACATTGATTGATCATTTGAAAGCTGTTAGGAGGTTTAGGTA
TGACGGGCTGAAGGATGCCCTGAAGGTACCCATAGGTAACCTTAAGCGACTATGGATCTGAT
CAGGGGCCCACCATGTAACACATGGGTAGAAGTCTTCGGACCTTGGGTTAAAAAACGTCTAG
GCCGCCCCCACAGGGATGTGGGGTTTCCCTTATAACCCCAATATTGTATAATGGCTGCATC
CAAAATGAATCCCGTTGGCAACCTGCTCTCCACAGTCTCCTCAACCGTTGGATCTCTTCTAC
AAAACCCTCTGTTGAAGAAAAGGAAATGGATTCTGACCGTGTTGCTGCCTCTACTACAACC
AATGCTGGTAATTTGGTACAAGCTTCTGTGGCCCCAACTATGCCTGTCAAGCCAGATTTTAA
AAACACAGATGATTTCTTGTCCATGAGCTACCGTTCAACAACAGCCCCAACCAACCCCACAA
AAATGGTTCACTTGGCACATGGCACTTGGACAACTAATCAGCACAGACAGGCATTGGTCGCA
TCAATTACTCTACCGCAGGCATTTTGGCCCAATCAAGATTTTCCGCATGGGGGCAGTCTCGT
TATTTTGCAGCAGTGCGCTGTGGCTTTCATATTCAAGTACAGTTGAATGTTAACATCGGTTC
TGCTGGTTGCTTGATTGCCGCGTACATGCCAAAGACGGCCCATGATCATATGAACACCTATA
CTTTTGGTTCTTACACCAACCTGCCACATGTTTTGATGAATGCGGCAACGACATCCCAGGCT
GATCTCTATATACCCTATGTTTTAATCATAACTATGCAAGAACTGATTCAGATGATTAGG
AGGCATTTACATTTGGGTTTGGTCAGCTCTCACAGTTCCATCAGGTTCACCTACAACAGTGG
ATGTGACCATTTTTGGTTCATTACTCGACTTGGATTTTCAGTGTCCTCGTCCTCCTGGTGCA
GACACAGTAATTTACACACAAGGGAAAAGAACTGTTCGAAAGACCAAGACATCAAAGTTCAA
ATGGGTCAGGAATAAAATTGACATAGCTGAAGGTCCAGGAGCAATGAACATCGCTAATGTTC
TCTCCACAACTGGTGGTCAAACTATTGCCTTGGTTGGTGAAAGAGCATTCTATGACCCAAGA
ACAGCTGGTGCTGCAGTGAGGTGCAAGGACCTCATGGAGATCGCCAGAATGCCAAGTGTGTT
CTTAGGAGAGAGTACTGAACCAGATGGTCGAAGGGGCTATTTCACCTGGTCACATACAATCT
CACCTGTTAATTGGGTTTTTGATGACCACATTTATTTGGAAAACATGCCCAATCTGAGATTA
TTCTCCTCCTGTTACAACTATTGGAGGGGCTCCTTTGTTATTAAACTGACAGTTTATGCGTC
AACTTTCAACAAAGGACGCTTGAGGATGGCATTTTCCCAAACAGAGAAGGCGCCTACACAC
AGGATGAAGCTCAGAACGCAATCTTTGTTGTGTGTGATATAGGCTTGAATAATACCTTTGAG
ATGACCATCCCCTACACTTGGGGCAACTGGATGAGACCAACAAGAGGAAACTCCTTGGGACA
TCTGAGGATTGATGTGTTGAACCGTCTTACATACAACAGTTCTTCCCCAAATGCAGTCAACT
GCATTCTTCAGATTAAGATGGGGGATGATGCAATGTTCATGGTGCCTACCACATCTAATCTA
GTTTGGCAAGGTCTGCACTCATGGGGTTCAGAAATGGACTTGGTGGACTCTCTCGACAATCC
AGACGAGATACAAGACAATGAGGAAATACAAACCCAAAATGTGGAGGCTGCACAAGGGGAAG
AAGCTGCGACTGAAGTTGGTCTTAGGGCAACAGAAAATGATGGCAGTCTTTCAGAACAATTG
AATATGAGTCAACCCATGTTCCTGAATTTTAAGAAGCATAAAGTCAACATCTATGCAGCATC
CCATACCAAAGTTGATCATATTTTTGGAAGAGCTTGGGCAGTGGGGTTTTTAACACAGAAA
CAGCTGCCATACAAAAATTTGATTTGCACTTTCCAACTTCTACTCATGGTGCATTGTCTAGA
TTTTTCTGCTTCTGGACTGGAGAGTTAAATATTCACATTTTGAATGTGTCAACCACAAATGC
CTTTTTGAAAGTTGCTCACACATGGTTTGGCACTGATTCTGGAATTGCCCGGACAGCTACTT
TGGAATCAAATGGAACAATGATTATACCACCAAACGAGCAAATGACACTTTGTGTACCCTAT
TATTCTGAGGTTCCATTAAGATGTGTTAAAGGTTCAGACAGGAATTCAGCCGGACTTGGTTC
TCTCTTCACACAGGCTGTGGGCAGAACAATCTCTAATCGGGTACAAATCTTTGTGAGCTTCC
GCTGTCCTAATTTTTCTTCCCACTACCTGCGCCCAGGGAAGCCACGTCTCGAAGCATATTG
GAACGAGTGGATGAAGCAAATGCGGAAGAACTTGAAGCTGTCTTGGAAGCTAGAACACCAGA
TGCACCGCTCCGCCTCAAGTTTAATCCAGAAGATCCTTTGAAACAATTGCGGGAGGCGGCCA
```

Fig. 7 Cont.

```
AGGCTTACTTTAATATAATGCACAGTGATGAAATGGATTTTGCCGGGGGGAAATTTTTGAAC
CAATGTGGTGACGTGGAAACCAACCCAGGCCCTGACATTGAGTTGGTCTATAAAAACAGAGG
CTTCTATAAGCATTATGGAGTTAGATTTGGTGGTCATATCTACCACTTGAATTCACAAGACA
TTCTGTCAACCGCAATTACAGGCAAGTCTGACTTCATTAAGGAAGAAGATGATGGCAAATGG
GTTCATGCTATGACAGCACCATTGGACTACTTACTGAAAAGTACATCAATTCAATGGTTGG
CTCCAAACACATCTTTTCCGCCACCTCCAATTGTGAGACCATTGCCAGAGATCTTTTCCCAG
GGAGAAAGGAAATAACTCAGTCCAAAGCCTTGGGGATTATTGGGTCATCTTGTTGTCAGCC
TCTCTTCTTTCATTGCTTGCTGTACCCTGGGATTATTCCTCACTTCAAACTGTTTATAACCA
ATCCATTGAAGGTGATGCTTCTGGCCTCACACTCCTAAGTCAAAGATGCATGACTTTTTTTT
CCAATACAATGTGTGAAACTTTTAATAATGATCTTGTTAAGTTTATTATTAAGATTTTGGTG
CGGCTTTTGTGCTACATCGTTCTTTATTGCCATGCACCAAATATGCTGACAACCATGTGTCT
GGGAACTCTTCTTGTTTTGGACATTACAACTTGTGAAATCTTGTCTGCTAACACCAAAGCAC
TCTTTCAGGCATTGGTTGATGGTGATGTGAAGAGTCTTGTCTGGAAAATTGCTGAGAATATG
CAATTTGCCCAATCCAAGGATGAACAAGCTGAGGACATGGCAGCAACCTTCAACTTTGCCTC
TGACATGGTTAATTTTGTGCCAATGGAACAGATGAGACAAGAAGGCTGGAGAGAATTTAATG
ATGTTTCTATGTCCTTTCGGCATGTTGAATGGTGGCTGACTATGTTCAAAAAGGTGTACAAT
GTTCTGAAAAGTATTTTTGCTCCTAGTATTGAACAGAAGGCTGTTGATTGGATAGATCGCAA
TCAAGAGTACATTGCCGATGTTTTGGACCATGCTTCCAACATCATCATAAAAATGAAGGATC
CAAAAGAACAGGGAGAGCATCAACCATTAGTGAATACTTTGAGGTTTTGAAACAACTAAAGC
CAATTGTGTCCCTTTGCATGAAGGTTGCCCCCTCCACTAAGTTTTCCTCTCAAGTGTTTAGA
ATCTATTCTGAAATGATGAGGGTCAATGTTAGAGTGCCTGCGAATACTGACTTGACTAGACT
GGAACCCATTGGCATTTGGGTTTCTAGTGAGCCAGGACAGGGTAAATCATTCTTTACACATA
TGTTGAGTACCTGTCTTCTGAAGTCCTGCAATTTAGAAGGAATTTATACCAACCCCACAGGT
TCAGAATTTATGGATGGCTATATTGGGCAGGACATTCATATCATAGATGATGCAGGGCAAAA
TAGAGAGGAAAAAGATTTGGCCTTGTTGTGTCAGTGTATTTCTTCTGTGCCTTTTACTGTTC
CAATGGCAGATTTGACAGAGAAGGGCACTTTTTATACAAGCAAAATTGTGATTGCCACCACC
AATAAATTTGATTTTACCTCAATGGTTTTGACAGATCCAGCAGCCCTTGAAAGGAGATTTCC
GTTCCACTTGCGCATTAGAGCTGTAGCCAGCTATTCGCGCAACAACAAACTAGATGTGGCCC
GTTCAATGGCGGCCATGGCAGATGGTTCTTGCTGGGAATATTCCACAGATGGTGGTAGGGCT
TGGAAGACCCTCTCCATGGATGAACTTGTGAAACAAATCACGGCAGTTTACACACAGAGGTC
AGATGCCCTTATGGTTTGGAAAAGGAAGTTGAATACCATCAGGAACGAAATGAGCCCTGGAT
CATCCACCGGCAGGATTTTTGAACCCTTAGAGGAAACACTCTGTGCTTTGGAACGTCGCTTT
GGTCAACTTGCTGATAGTCTTAAAGACAACTATCATAAAACAGCTGATGAGTTGATTGAAGC
TATAGAAGATATGATGGCACCGTCACAGAGCCCTTTTGCATGCTTTGCTGAATCCTATCGAC
CCACCATTAAATATACTGCCAGTGATAAAGTTAAATCATGGGTTAAAAATCATATGAATAGA
TGGAAAGAATTTGTAATGAGAAATAAAGGCTGGTTTACACTTTTTTCTGTGCTCTCATCATT
TCTCTCGATTCTTACTCTTGTCTATTTACACTATAAAAAGGAGAAGAAAGAGGAAGAGAGAC
AGGAGCGGGCTTACAACCCTCAAACTGCAATTTCTAAGAAGGGGGGTAAGCCTAAGCTCTCA
TTAGTGAAAACCACAAACTTTGTTAATGAAGCACCCTATATGCAAGATCTTGAACATTGCTT
TGCACAAACGGCCTACATTTCTTCTCCAGAAACCCAAGATATAATACATTGTGCTGCCTTGA
GTGAAGACACCATTTTGGTTTATGGACATTCTCAGTTTTATTTTAACCGCTATGAGGACCTG
CGGTTACATTTTAAAGGGGCCATTTTTCCCATAGAAGGGGGAAAAATTTCTCAAGTTACCGT
GAATGGACAGCCTATGGATTTGATACTTGTGAAGATAGATAAACTTCCAATAACATTTAAAA
ATTATACAAAATATTATACAACTGAGGTTGGCAAGGAAACTCTTTTAATTTGGAATTCAGAA
AAGGGCAGGTTGGCCATGCCTGTTCAATGTGTGGCTCCGGCTGGTCCGGTGGAGACAATGGA
AGGAACAATTACTCATAAGACCTATTCATATAAAGTGGCATCAAAAAAAGGAATGTGTGGGG
GCCTTTTGGTCACTAGAGTGCATGGCACATTCAAGGTTCTGGGAATGCACATTGCAGGCAAT
GGGCAAGTTGCACGAGCTGCAGCAGTTCACTTTATATCCAATGGTGCAGCTGGCTTTATGGA
TCAAGGTGTTGTTGTGGCCAAAGAAAAGTTACAAAAGCCCATTTATTTGCCATCTAAGACAG
CTTTGAATCCCAGTCCCTTGAATGGTGTAGTCCCCGTGAAAATGGAACCAGCTGTGCTTAGT
CCTCATGACACCAGGCTTGAAGTCATCATGCCCAGCGTTGTGAAAACAGCGGCAGCTAAGTA
TAGAGTTAATATTTTTAATCCTGATTTTGAGATTTGGGAGAGAGTGGTGGATGAGTTAAAAT
```

Fig. 7 Cont.
CAAAGTTTAGAACCAAACTTGGAATTCATAAACATGTCTCTTTTCAGAAAGCAGTTCAGGGT
TTCTCCTCCCTTTCATCTCTTGATCTTTCCACATCCCCAGGACAAAAGTATGTTGAAAAGGG
TATGAAGAAGAGATCTTTTGTCCACTGAGCCATTTTGGATGCATCCTCAATTGGAAGGTG
ATGTTAAAGATATACTTGGGGCCGTTTACTCTGGTAAAAAGCCCCATACATTTTTTGCTGCA
CATTTGAAAGATGAGTTGCGCAAAAAAGAAAAGATTGCGCAAGGAAAGACCCGCTGCATTGA
AGCCTGTTCAATTGACTATGTGATTGCCTACAGAGTTGTAATGTCCTCACTCTATGAGGCAA
TCTATCAAACTCCGGCTCAGGAGTTGGGCCTGGCAGTGGGAATGAATCCCTGGACAGATTGG
GATCCAATGATCAATGTTTTGCAGCCATATAACTATGGCCTGGATTACTCATCTTATGATGG
CAGCCTTTCTGAACAACTGATGAGATATGGAGTGGAAATACTTGCCTACTGTCATGAACAAC
CAGAGGCTGTAATGATTCTTCATGAACCTGTTATAAACTCTCAACACCTTGTGATGGATGAA
ATCTGGCATGTGAATGGTGGAATGCCCTCAGGGGCCCCATGTACAACTGTGCTAAATTCCAT
ATGCAATCTGCTAGTTTGTACATATTTGGCCTATGAGCAGAGCTTGGATATTGAGGTGTTAC
CCATTGTTTATGGAGATGATGTAATTTTTTCTGTTTCATCCCCTTTGGATGCTGAATACTTG
GTTCAGAGTGCAGCCCAAAATTTTGGAATGGAAGTGACCTCATCAGATAAATCTGGTCCCCC
TAAACTTTTGAAAATGGATGAGATTGAATTTTAAAGAGGACAACAAAATTTTTTCCTGGCT
CCACCTACAAGGTGGGGCCTTGAGCCTGGATACCATGGAACAACATATTATGTGGATGAAG
AATTTGGAAACCTTTCCAGAACAACTTGTTAGTTTTGAGAATGAATTGGTGTTGCATGGGAA
AGAAATTTATGATGATTATAAAAATAGGTTTAATCCTATTTTGAATCAATGGCGAGTGTGCA
TGCAGGACTATGAAGTGGCCCTGCATCGCATGCTACGCTATGTTTTTGATTGAATTGATTTA
GTTTGATTTTGATTTTATTAGCTTTAGTTTATGTAAGTTAGAATTAGATTATTTTAGTTTAG
TTTTAAAGATTTTGATTTGATTGAATTTGGCCCACCAATC Fig. 8 (SEQ ID NO. 2)

```
TTTGAAAGGGGTCTCCTGGTGGGGTGGGTACGTCTCTCGCTCATTGAGTGGGGGCGTGGCTC
ACCAACCACACCTGGTTGGTCCCCAGGTTCATGCAATAACCACTTTTTGTAATCTTTACATC
TAAGCTTAATTCACCCACTAGAACTGGACGAAACCGCTTGGAATAAGTTTGGTTCTCTCTTG
AGTGTGTTTTGTGTTAGCATAATTTCTGTCTCTAGAGTGCTTTACACTCTAGTAGGGCTGT
ACCCGGGCGGTCCCACTCTTCACAGGAATCTGCACAGGTGGCTTTCACCTCTGGACAGTGCA
TTCCATACCCGCTCCACAATAGAAGATGATGTATATCTTTGTTTGTGAAATGCTCATGAAAC
GTGTGTGTAGGCGTAGCGGCTACTTGAATGCCAGCGGAACCCCCCTAGTGGTAACACTAGCC
TCTGGGCCCAAAAGGCATGTCTCTGACCATTCAAGTACACAACCCCAGTGATACACATTT
AGTAATGGCTCAGTAATGGACATTGATTGATCATCAGACAATTGTTAGGAGGCCTAGGTATG
ACGGGCTGAAGGATGCCCTGGAGGTACCCGCAGGTAACCTTAAGAGACTGTGGATCTGACCA
GGGGCCCACCATGGAAACATGGGTAGAAGTCTTCGGACCTTGGGTTAAAAAACGTCTAGGCC
CGCCCCCACAGGGATGTGGGGTTTCCCTTATAACCCCAATATCACATTATGGCTGCAACCA
AGATGAATCCCGTTGAGAATCTTCTTTCTACTGTCTCCTCCACCGTTGGCTCACTGCTACAA
AATCCCACCATGGAAGAAAAGGAAATGGACTCAGATCGTGTTGCGGCATCCACCACTACTAA
CGCTGGAAATGTAGTTCAGGCTTCAGTTGCCCCCACCATGCCAATTAAACCAGATTTCAAGA
ACACGGATAACTTTTTGTCAATGAGTTATAGCCCAAATACTGCACCTACAAATCCAACAAAA
ATGGTACATTTGGCTAATGGAACATGGACTACATCGCAGCATCGACAGTCTTTGGTTGCATC
GATTCAGCTACCACAGGCATTTTGGCCCAATGAACGCTATCCGGCTTGGGGTCAATCACGCT
ATTTTGCTGCAGTCCGATGTGGCTTTCATATTCAGGTTCAATTGAATGTTAACATTGGCTCA
GCAGGTTGTTTGATAGCTGCCTATATGCCCAAAAGTGCACATGATCATATGGATACATATAC
ATTAGTTCCTACACCAATTTGCCTCATGTTCTGATGAATGCTGCCACCACGTCTCAGGCTG
ATTTGTATATACCCTATGTGCATAATCATAATTATGCAAAGACAGATTCAGATGACTTGGGT
GGTATATACATTTGGTGTTGGTCTGCCCTCACAGTTCCATCAGGTTCTCCGACAACTGTTGA
TGTCACAATTTTTGGCTCCTTGCTTGACTTGGACTTCCAGTGCCCTAGACCACCAGGTGCTA
ATACTGTCATATTTACACAAGGCAAAAGAACTGCCAGGAAAACCAAAGCAACAAAATTTAAA
TGGACAAGGAATAAAATAGACATTGCTGAAGGTCCTGGCGCTCTTAATATTGCCAATGTCTT
GTCTACTACAGGGGGCCAAACTGTTGCCCTCGTTGGGGAAAGAGCTTTCTACGATCCCAGAA
CTGCAGGAGCCGCTGTGCGGTGTAAGGATTTGATGGAAATTGCCAGAATGCCATCAGTCTAT
AAGGGGGAGAGAACTGAACCTGGAGGAACTAATGGCTATTTTCAATGGTCTCATACGCACTC
CCCTATAAATTGGGTTTTTGACGGGGGAATTCATTTGGAAGACATGCCCAATCTAAATTTGT
TTTCCTCATGCTATAACTATTGGAGAGGCTCAATTGTTTTGAAACTCACTGTGTATGCATCA
ACCTTTAACAAGGGTAGATTGAGAATGGCCTTCTTCCCAAATCATGATGCAAGGTACACAGA
GGAAGAAGCACAAAATGCCATCTTCATGGTGTGTGATATTGGGCTCAACAACACTTTTGAAA
TGACCATCCCATACACCTGGGGAAACTGGATGAGACCAACTAGGGGATCTGTCATTGGATGG
CTTAGGATTGATGTTTTGAATCGCCTCACTTATAACAGTTCCTCACCCAATGCTGTTAATTG
CATTCTTCAGGTTAAAATGGGGAATGATGCCAAATTTATGGTACCCACCACATCTAACATTG
TGTGGGAAGGTCTCCACTCATGGGGGTCTGAGATGGACTTACTGGACAGTTTGGATAATCCA
GAAGAGATTCAAGATATGGAGGAACCAGAATCTGAAAATGTGGAGGCCGCACAAGGAGAGGA
AGCCGCCACTGCCGTTGGCCTTCGAGCCACCGAAAATGATGGATCCCTATCTGAACAACAAA
ACATGGCACAACCAATGTTTTTGAATTTTAAGCAACATAGAGTGGACATTTACTCTGCTTCC
CACACCAAAGTTGACCATATTTTGGTAGGGCGTGGGCAGTGGGAATTTTAATGTGACTAA
TGCTAATATATCCAAATTTGACCTTAACTTTCCACAACCACACATGGTGCATTGTGTCGCT
TCTTCTGTTTCTGGACGGGAGAGCTTAACTTGCATATTTTGAACATTTCTTCTTCCAATGCT
CCAGTCAAAGTTGCTCACACATGGTTTGGCACAGATTCAGGCATTGCCAGGACTGCAACTTT
GGAATCAAACGGGGTTATCATCATACCACCAAATGAGCAAATGACACTCTGCATACCCTATT
ATTCTGAGGCACCATTGCGCTGTGTTAAGGGGCCACATTCAGCTGGTGCTGGATTGGGCTCA
ATTTTCACACAGTGTATTGGCAACAGCGTTAATAACAGGATTCAAATTTTTGTTAGTTTTCG
CTGCCCAAACTTCTTTTTTCCCCTTCCTGCACCCCATGAGGCTTCTTCAAGGTCAATTTTGC
AGAGAATTTCCACTGCTAGCGCAGATGAGTTAGAAGCTGTCTTGGACGCAAAAACACCTGAT
```

Fig. 8 Cont.

```
GCTCCTGTGCGCTTGTGCTACCAACCAGAGGATCCTTTGAGACAACTTAGGGAGGCAGCTAA
GGCATATTTCAATATTATGCACAATGATGAGATGGACTATTCTGGAGGTAAATTCTTGAATC
AGTGTGGTGATGTGGAGTCCAATCCAGGTCCTGATATTGAATTAGTCTATAAGAACAGAGGC
TTTTATAAACATTATGGGGTTAGGTTTGGTGGCTTTATTTACCATCTTAATTCACAAGACAT
TTTGTCGACAGCCATCACTGGAAAATCAGACTTCATAAAAGAGGAAGATGATGGTAAATGGA
CACATGCTATGACTGCACCCCTGGATTATTTTACTGAGAAGTATGTGAAATCAATGGTTGGT
TCAAAACACATTTTTTCCGCCACATCAAATTGTGAAACCATTGCCAGGGATTTGTTTCCAGG
AAAGAAGGAGATTAGTCAATCTAAAGCTTTGGGTATTATTGGTGTGATCCTTCTTTCTGCAT
CTCTTTTATCCCTACTTGCCGTTCCATGGATTATTCCTCACTTCAGACAGTTTATAATCAA
TCAATTGAAGGGGATGCTTCAGGCTTAACACTTTTGAGCCAGAGATGCATGACTTTTTTTC
CAATACCATGTGTGAAACTTTTAATAATGATCTTGTGAAGTTTATAATTAAGATTTTAGTTA
GGCTTCTTTGCTATATTGTTCTTTATTGTCATGCCCCTAATATGCTTACAACAATGTGTTTA
GGCACCCTTTTGGTTTTGGATATTACCACATGTGAGATTTTATCAGCCAATACAAAGGCCCT
GTTTCAAGCTCTTCTTGATGGAGACGTCAAGAATTTGGTTTGGAAGATTGCAGAGAACATGC
AGTTTGCCCAGTCTACAGATGAGCAGGCAGAGGAAATGGCTGCCACCTTTTCATTTGCCAAA
GACATGGTTGACATTCATCCAATTGGGGCTGAGCCATTTCAAAACCAAGGCTTTAGGGAGTT
TAATGATGTGTCAATGTCCTTTCGCCACATTGAATGGTGGCTTACAATGTTTAAGAAAGTTT
ACAATGTTCTTAAGGGCATTTTCTCTCCATCCATTGAGCAGAAAGCGGTGGCGTGGTTGGAT
CGCAACCAAGAATATGTTGCATCAATCTTAGATCATTGCTCTGACATGATTATCCGCATGAA
AGACCCAAAACAACAGCGGAACCCCAAGACCATTGAAGAATATTTTGATGTGTTAAAGAAAA
TGAAGCCCTTGGTGTCACTCTGCATTAAAGTTGCCCCGTCAACAAAGTTTTCATCCCAAGTG
TTTAGGTTGTATTCAGAGCTAATGAAGGTTAATGTTAGAGTGCCGGTTAACACAGATCTCAC
ACGCATTGAGCCAATTGGTGTGTGGATCTCCAGTGAGCCAGGTCAGGGAAAATCTTTCTTTA
CTCACATGCTTAGCACTTCACTTTTGAAAAGTTGTAATTTGGATGGGGTGTATACCAATGCC
ACAGGCTCTGAGTTTATGGATGGATATGTTGGTCAAGATATACACATTATTGATGATGCAGG
ACAAAATCGGGAAGAGAAGGATTTGGCTCTGCTGTGCCAGTGCATCTCATCTGTGCCATTTA
CTGTACCTATGGCTGATCTAACAGAGAAAGGGACATTTTATACCAGCAAGATTGTTATTGCC
ACAACCAACAAGAGTGATTTCAATTGCATGGTTTTGACAGATCCAGCTGCTCTAGAGAGGCG
TTTCCCATTTAATTTGAGAATTAGGGCAGTTAAAAGTTTTATGAATAAGGACAGAAAGTTGG
ATGTGCCAAGATCAATGGGAGCCATGGCAGATGGATCCTGCTGGGAGTGCTCTATGGACTAT
GGCAGAACCTGGAACACCGTGGTGATGAGAGATCTTGTGAAACAAATAACAGAAATGTATAA
ACAAAGAGATGATGCCCTGACTGTTTGGAAGTATAAGTTAAATCAGATTAGGAATGAGATGT
CCCCTGGTGACTCAATTGGCCGCATTCTCGATCCAATGGAGGAGACACTCTGTTCATTGGAG
CGCAGGTTTGGCCAGTTGGCAGATAGTCTTAGAGAAAATTACCATAGGACAGCTGATGAACT
AATTGAAGTTATAGAAGACATGATGGCACCAGGGAATAGTCCCTTTGCATGCTTCGAAAGTG
TAGCACCATCACTTAAACCAAGAACAGCTTGTCAAAAAGTTAAAGATTGGGTAAAACAACAC
ATGATTAGATGGGGCAACTTTGTGATGAGGAATAAAGGCTGGTTTACACTTTTTTCTGTACT
TTCATCTTTTCTTTCAATTCTTACTCTTGTTTATTTACATTATAAAAAGAGAAAAAGAGG
AAGAAAGACAAGAGCGGGCTTACAACCCTCAAACTGCAACTCCCAAGAAGGGGGGTAAGCCA
AAGCTCTCTTTGGTAAAAACTACAAATTTTATAAATGAGGCACCATATATGCAGGATTTGGA
ACACTGCTTTGCCCAAACAGCCTACATTTCATCCCAGAGACTCAGGATATAATTCATTGTG
CTGCCTTGTGTGAGGATACCATTTTGGTTTATGGACATTCACAATTTTATTTTAACCGCTAT
GAAGATTTGCGGTTACATTTTAAAGGAGCCATTTTTCCTATTGAGGGTGGAAAAATTTCACA
AGTTACTGTGAATGGGCAGCCGATGGATTTGATTCTTGTTAAAATAGACAAACTTCCCATAA
CCTTTAAAAATTATACCAAATATTACACAACTGAAATTGGGAAGGAAACTCTTTTAATTTGG
AATTCTGAGAAAGGGAGACTGGCTATGCCAGTCCAATGTGTTGCCCCGGCTGGACCGGTGGA
AACAATGGAAGGCACCATCACTCATAAAACCTATTCCTACAAAGTGGCATCAAAGAAAGGCA
TGTGCGGTGGACTCCTAGTTACTAGAGTGAATGGAACATTTAAGGTTTTGGGGATGCACATT
GCTGGGAACGGACAGGTTGCGCGGGCCGCAGCAGTTCACTTCATTTCAAATGGGGCTAGTGG
TTTTATGGATCAGGGGGTTGTGGTTGCAAAAGAGAAGATGCAGAAACCAATTTATTTGCCAT
CTAAAACAGCACTAAATCCTAGCCCTTTGAATGGTGTTGTGCCCGTGAAGATGGAGCCTGCA
GTTCTTAGCCCTCATGATGTTAGACTTGAAGTGATTATGCCAAGCGTGGTTAAAAATGCAGC
```

Fig. 8 Cont.
AGCCAAGTACAGAGTTAACATCTTCAACCCAGATTTTGAAATCTGGGAGAGGGTGGTTGATG
AATTGAAAGCAAGGTTTCGATCTAAGCTTGGCATACACAAACATGTTTCTCTTCAAAAGGCT
GTGCAAGGTTTTTCCTCCCTTTCGTCTCTTGATCTTTCTACCTCTCCAGGGCAAAAGTATGT
TGAAAAAGGAATGAAGAAAAGGGATCTTTTGTCCACTGAACCATTTTGGATGCATCCTCAAT
TGGAAAGTGATGTTAAAGATATACTTGGGGCAGTTTATTCTGGTAAGAAACCCCACACATTT
TTTGCTGCCCACTTGAAAGATGAGTTGCGCAAGAAGGAAAAGATTGCGCAAGGAAAGACCCG
CTGCATTGAAGCATGTTCAATTGATTATGTTATTGCCTATAGAGTTGTGATGTCCTCTCTCT
ATGAGGCAATTTATCAAACCCCAGCTCAAGAATTGGGCTTGGCAGTGGGAATGAATCCCTGG
ACAGATTGGGATCCAATGATTAATGTTTTGCAGCCTTATAATTATGGTTTAGATTATTCATC
CTATGATGGCAGTCTTTCTGAACAGTTAATGAGATATGGTGTTGAAATACTTGCTTATTGTC
ATGAGCAACCAGAAGCTGTGATGATTCTCCATGAGCCAGTTATAAATTCGCAACACCTTGTG
ATGGATGAAATCTGGCATGTAAATGGAGGAATGCCCTCAGGAGCCCCATGTACAACTGTGCT
AAACTCTATATGTAATTTGCTGGTTTGTACATATTTGGCTTATGAGCAGAGTTTGGACATTG
AGGTGTTGCCTATTGTTTATGGGGATGATGTGATTTTTTCTGTTTCTTCACCATTGGATGCT
GAATATTTGGTTCAGAGCGCTGCCCAAAATTTTGGAATGGAAGTGACATCATCAGATAAATC
TGGCCCCCCAAAACTTTTGAAAATGGATGAGATTGAATTTTTAAAGAGGACAACAAAATTTT
TTCCCGGCTCCACCTATAAGGTGGGGGCCTTGAGCCTGGATACCATGGAACAACACATTATG
TGGATGAAGAATCTGGAAACCTTTCCAGAACAACTTGTTAGCTTTGAAAATGAGTTGGTGTT
GCATGGGAAAGAAATTTATGATGATTATAAAAATAGGTTTAATCCTATTTTGAATCAATGGC
GAGTGTGCATGCAGGACTATGAAGTGGCTCTGCATCGCATGCTACGCTATGTTTTTGATTAG
ATTGATTTAGTTTGATTTTGATTTTATTAGTTTTATTTTAGGTTAGAATTAGATTATTTTAG
TTTAGTTTTAAGGATTTTGATTTGATTGAATTTGGCCCACCAATC Fig. 9  (SEQ ID NO. 3)

```
TTTGAAAGGGGTCTCCTGGTGGGGTGGGTACACTCCTCGCTCAATGAGTGGGGGTGTGGCTC
ATTGCCCACACCTGGTTGGTTCCCAGGTTCATACAATAACCATCAATAAACTTCTCAACATC
TAAGCTACTACTATCCCACACTAAACTGGACGAAGCCGCTTGGAATAAGTCTAGTTTCATTC
TGTGTGTGTTTTGCACTGAAATTATTTCTGTCTCTGGGGTGCTTTACACTTCAGTAGGGCT
GTACCCGGGCGGTCCCACTCTTCACAGGAATCTGCACAGGTGGCTTTCACCTCTGGACAGTG
CATTCCACACCCGCTCCACAGTAGAAGATGATGTGTGTCTTTGCTTGTGAAAAGCTTGTGAA
AATCGTGTGTAGGCGTAGCGGCTACTTGAGTGCCAGCGGACTACCCCTAGTGGTAACACTAG
CCTCTGGGCCCAAAAGGCATGTCAATTGACCACTCAGGTACACAACCCCAGTGATGCACACG
TCTAGTAACGGCTTAGTAACGAGCATTGATTGATCATTTGAAAACTGCTAGGAGGTTTAGGT
ATGACGGGCTGAAGGATGCCCTGAAGGTACCCATAGGTAACCTTAAGCGACTATGGATCTGA
TCAGGGGCCCACCATGTACTACATGGGTAGAAGTCTTCGGACCTTGGGTTAAAAAACGTCTA
GGCCCGCCCCCACAGGGATGTGGGGTTTCCCTTATAACCCCAATATTGTATAATGGCTGCA
TCCAAAATGAATCCCGTTGGCAACCTGCTTTCCACAGTCTCCTCAACCGTTGGATCTCTTCT
ACAAAACCCTCTGTTGAAGAAAAGGAAATGGATTCTGACCGTGTTGCTGCCTCCACCACGA
CCAATGCTGGTAATTTGGTGCAAGCTTCTGTGGCTCCAACCATGCCTGTAAAACCAGACTTT
AAGAACACAGATGACTTCTTGTCCATGAGCTACCGCTCAACAACGGCCCCAACCAACCCGAC
AAAAATGGTTCACTTAGCGCATGGAACTTGGACAACTAATCAGCACAGACAGGCATTGGTTG
CATCAATTACCCTACCACAGGCATTCTGGCCCAATCAAGATTTTCCAGCATGGGGGCAATCT
CGCTATTTTGCAGCAGTGCGCTGTGGCTTTCATATACAAGTGCAGTTGAATGTTAACATTGG
TTCTGCCGGCTGCTTGATTGCCGCATACATGCCAAAGACGGCCCATGATCATATGGGTACCT
ATACTTTTGGCTCCTACACCAACCTGCCACATGTTTTGATGAATGCAGCAACGACATCTCAG
GCTGATCTCTATATACCCTATGTTTTTAATCACAATTATGCACGAACTGATTCAGATGACTT
AGGAGGTATTTACATTTGGGTATGGTCAGCTCTCACAGTTCCATCAGGTTCACCTACTACAG
TGGATGTCACCATTTTTGGTTCATTACTCGACTTAGATTTTCAATGTCCTCGTCCCCCTGGA
GCAGCCACAGTAATCTACACACAAGGGAAAAGAACTGTTCGAAAGACCAAAACATCAAAGTT
TAAATGGGTCAGGAATAAAATTGACATAGCTGAAGGCCCAGGAGCAATGAACATTGCTAATG
TTCTCTCCACAACTGGCGGTCAAACTATTGCCTTGGTTGGTGAAAGAGCATTCTATGACCCA
AGAACAGCTGGTGCTGCAGTAAGGTGCAAAGATCTCATGGAGATCGCCAGAATGCCGAGTGT
GTTCTTGGGAGAGAGCACTGAACCAGATGGTCGAAGAGGCTATTTTACCTGGTCACATACAA
TCTCACCTGTTAATTGGGTCTTTGATGATCATATTTATTTAGAAAATATGCCCAATTTGAGA
TTGTTTTCCTCTTGTTATAATTATTGGAGAGGGTCTTTTGTTATTAAATTAACAGTCTATGC
ATCAACTTTCAACAAAGGACGCTTGAGGATGGCATTCTTCCCAAACAGAGAGGGCGCCTACA
CACAGGATGAAGCCCAGAATGCAATCTTTGTTGTCTGTGATATAGGCCTGAATAACACTTTT
GAGATGACCATCCCCTACACTTGGGGCAATTGGATGAGGCCAACAAGAGGGAATTCCTTGGG
ACATTTGAGGATTGATGTGCTGAATCGTCTCACATACAACAGTTCCTCCCCGAATGCAGTCA
ACTGCATTCTTCAGATCAAGATGGGAGATGATGCAATGTTTATGGTGCCCACCACATCTAAT
CTAGTTTGGCAAGGCCTACATTCCTGGGGTTCAGAAATGGACCTGGTGGACTCCCTTGACAA
TCCAGAAGAGATACAGGATAATGAGGAAATACAAACTCAGAATGTGGAGGCAGCACAAGGGG
AAGAAGCTGCAACAGAAGTTGGACTTAGGGCTACAGAAAATGATGGTAGTCTTTCAGAACAA
CTGAATATGAGTCAACCCATGTTCTTGAATTTCAAGAAGCATAAAGTTAACATCTATGCAGC
ATCTCACACTAAAGTTGATCATATTTTTGGCAGAGCTTGGGCAGTAGGAGTTTTTAATACAG
AAACAGCTGCCATACAAAAATTTGATTTGCATTTTCCAACTTCTACCCATGGTGCATTATCT
AGATTTTTCTGTTTTTGGACTGGAGAACTGAACATTCACATCTTGAATGTGTCAACCACAAA
TGCATTCTTGAAAGTTGCTCACACATGGTTTGGCACTGATTCTGGAATTGCTCGGACAGCCA
CTTTGGAATCAAATGGAACAATGATTATACCACCAAATGAGCAAATGACACTCTGTGTGCCC
TATTATTCTGAGGTCCCATTAAGATGTGTTAAGGGCTCAGACAGGAATTCAGCCGGTCTTGG
TTCTCTTTTCACACAAGCTGTAGGCAGAACAATTTCCAATCGGGTTCAAATTTTTGTGAGCT
TCCGCTGTCCTAATTTTTTCTTCCCACTACCCGCGCCCAGAGAAGCCACGTCCCGAAGCATA
```

Fig. 9 Cont.

```
TTGGAACGAGTGGATGAAGCGAATGCAGAAGAACTTGAAGCTGTTTTGGAAGCTAGAACACC
AGATGCGCCGCTCCGCCTCAAATTTAATCCAGAAGACCCCTTGAAACAATTGCGGGAAGCGG
CTAAGGCCTACTTTAATATAATGCACAGTGATGAAATGGATTTTGCCGGGGGGAAATTTTTG
AATCAATGTGGTGATGTGGAAACTAACCCAGGCCCTGACATTGAGTTGGTCTATAAAACAG
AGGCTTTTATAAACATTATGGGGTTAGATTTGGTGGCTATATCTACCATTTGAATTCACAGG
ATATTCTGTCAACTGCAATTACAGGCAAGTCTGATTTCATTAAGGAGGAAGATGATGGCAAA
TGGGTTCATGCTATGACGGCACCACTGGATTATTTTACTGAAAAGTACATCAATTCAATGGT
TGGTTCCAAACATATTTTTTCCGCCACCTCCAATTGTGAGACCATTGCCAGAGACCTTTTCC
CAGGGAGAAAGGAAATAACTCAGTCCAAAGCCTTGGGAATTATTGGGTCATTTGTTGTCA
GCCTCTCTTCTTTCCTTGCTTGCTGTACCCTGGGATTATTCCTCACTTCAAACTGTTTATAA
CCAATCCATTGAAGGTGACGCTTCTGGCCTCACACTTTTAAGTCAAAGATGCATGACTTTTT
TTTCTAACACAATGTGTGAAACCTTTAATAATGATCTTGTTAAGTTTATTATTAAGATTTTG
GTGCGGCTTTTGTGCTACATCGTTCTCTATTGCCATGCACCAAATATGCTGACAACTATGTG
TCTGGGAACTCTTCTTGTTTGGACATTACAACTTGTGAAATCTTGTCTGCCAACACCAAAG
CACTCTTTCAGGCATTGGTCGATGGTGATGTGAAGAGTCTTGTCTGGAAAATTGCTGAAAAC
ATGCAGTTTGCCCAATCCAAAGATGAACAAGCAGAGGAAATGGCGGCAACCTTCAACTTTGC
TTCTGATATGGTTAATTTTGTGCCAATGGAACAGATGAGACAAGAAGGCTGGAGAGAATTTA
ATGATGTTTCTATGTCCTTCCGGCATGTAGAATGGTGGCTGACCATGTTTAAAAAAGTGTAT
AATGGTCTGAAAAGTATTTTTGCACCTAGTATTGAACAGAAGGCTGTTGATTGGATAGATCG
CAATCAAGAATATATTGCCGATGTTTTGGACCATGCTTCCAACATCATTATAAAAATGAAGG
ACCCAAAAGAACAGCGGAAAGCATTAACCATTAGTGAATACTTTGAAGTTTTGAAGCAATTA
AAGCCAATTGTGTCTCTTTGCATGAAGGTTGCTCCCTCCACTAAGTTTTCCTCTCAAGTGTT
TAGAATTTATTCTGAAATGATGAAGGTTAATGTTAGAGTGCCTGCAAATACTGACTTGACCA
GATTGGAACCCATTGGCATTTGGGTTTCTAGTGAGCCAGGACAGGGTAAATCATTTTTTACA
CACATGTTGAGCACCTGCCTTTTAAAATCCTGCAATTTAGAGGGAATTTATACCAACCCCAC
TGGGTCAGAATTTATGGATGGTTATATTGGACAGGACATCCATATTATAGATGATGCAGGGC
AAAACAGGGAGGAAAAGATTTAGCCTTGTTGTGCCAGTGTATTTCCTCTGTGCCTTTTACC
GTCCCAATGGCAGATTTGACAGAGAAGGGCACTTTTTACACAAGTAAAATTGTGATTGCTAC
CACCAATAAATTTGATTTTACATCAATGGTTTTGACAGATCCAGCAGCTCTTGAAAGGAGGT
TCCCGTTTCATTTGCGCATTAGAGCTGTAGCCAGCTACTCGCGCAATAATAAATTAGATGTG
GCCCGCTCAATGGCAGCCATGGCTGATGGCTCTTGCTGGGAATACTCTACAGATGGTGGTAG
GGCTTGGAAGACTCTGTCCATGGATGAACTTGTGAAACAGATTACGGCAGTCTATACACAGA
GATCAGATGCCCTTATGGTTTGGAAAAGGAAGTTAAACACCATTAGGAATGAAATGAGTCCT
GGATCCTCCACCGGTAGGATCTTTGAACCCTTGGAGGAAACACTTTGTGCTCTGGAACGCCG
CTTTGGTCAACTTGCTGATAGCCTTAAAGACAATTACCACAAAACAGCTGATGAGCTGATTG
AGGCTATAGAAGATATGATGGCACCATCACAGAGCCCTTTTGCATGCTTTGCAGAATCCTAT
CGGCCCACCATTAAATACACTGCCAGTGATAAAGTTAAATCCTGGGTCAAAAATCATATGAA
TAGATGGAAAGAGTTTGTAATGAGAAATAAAGGCTGGTTTACACTTTTTTCTGTGCTTTCAT
CTTTTCTTTCAATTCTTACTCTTGTTTACTTGCATTATAAAAAGGAAAAGAAAGAGGAAGAG
AGACAAGAGCGAGCTTACAACCCTCAAACCGCAACTTTTAAGAAGGGGGGTAAGCCCAAGCT
CTCATTGGTGAAAAATACAAATTTTGTTAATGAAGCACCCTATATGCAAGATCTTGAACACT
GTTTTGCACAAACAGCCTACATCTCATCTTCAGAGACCCAGGATATAATACATTGTGCTGCT
TTGAGTGAAGACACCATCTTGGTTTATGGACACTCCCAGTTTTATTTTAACCGCTATGAAGA
TCTGCGGTTGCATTTTAAAGGGGCCATTTTTCCTATAGAAGGGGGGAAAATCTCTCAAGTTA
CTGTGAATGGGCAGCCCATGGATTTAATTCTTGTGAAAATAGATAAACTTCCAATAACATTT
AAAAATTATACAAAGTACTATACAACTGAGGTTGGTAAGGAAACACTCTTAATTTGGAATTC
AGAGAAAGGCAGATTGGCTATGCCTGTTCAATGTGTAGCCCCGGCTGGTCCGGTGGAAACAA
TGGAAGGAACAGTCACCCACAAGACCTATTCATACAAGGTGGCATCAAAAAAGGAATGTGT
GGGGGTCTCTTGGTTACTAGAGTGCACGGCACATTTAAGGTTTTAGGAATGCACATTGCTGG
CAATGGACAAGTTGCACGAGCCGCAGCAGTCCACTTTATATCCAATGGGGCTGCTGGCTTTA
TGGATCAGGGTGTTGTTGTGGCCAAGGAAAAATTGCAGAAGCCCATTTATTTGCCATCCAAG
ACAGCCTTGAATCCTAGTCCCTTGAATGGAGTAGTTCCTGTGAAAATGGAGCCAGCTGTGCT
```

Fig. 9 Cont.
TAGTCCTCATGATACCAGGCTTGAAGTTGCCATGCCCAGTGTTGTGAAAACAGCAGCAGCCA
AGTATAGAGTTAACATTTTCAACCCTGACTTTGAGATTTGGGAGAGAGTTGTGGATGAGCTA
AAGTCAAGGTTTAGATTTAAACTTGGGATTCATAAACATGTTTCTTTCCAAAAAGCAGTTCA
GGGTTTTTCTTCTCTTTCATCTCTTGATCTTTCCACTTCTCCAGGACAAAAGTATGTTGAAA
AAGGCATGAAGAAGAGAGATCTTTTATCCACTGAACCATTTTGGATACATCCTCAATTGGAA
AATGATGTTAAAGATATACTTGGGGCTGTTTATTCTGGCAAAAAACCCCATACATTTTTTGC
TGCCCATTTGAAAGATGAATTGCGCAAAAAAGAAAAGATTGCACAAGGCAAGACCCGCTGCA
TTGAAGCCTGCTCAATTGACTATGTGATTGCCTATAGAGTTGTAATGTCCTCTCTCTATGAG
GCAATCTATCAAACCCCAGCTCAGGAATTAGGCTTGGCAGTGGGGATGAATCCCTGGACAGA
CTGGGATCCAATGATTAATGTTTTGCAACCATATAATTATGGTTTGGATTATTCATCTTATG
ATGGCAGTCTTTCTGAGCAGCTGATGAGGTATGGTGTGGAAATACTTGCCTATTGTCATGAA
CAACCAGAGGCTGTGATGATTCTTCATGAACCAGTTATAAACTCACAACACCTTGTGATGGA
TGAAATTTGGCATGTAAATGGAGGAATGCCCTCAGGAGCCCCATGTACAACTGTGCTAAATT
CYATATGCAATCTGCTGGTTTGTACATATTTGGCTTATGAGCAAAGTTTGGATATTGAGGTG
TTGCCCATTGTTTATGGAGATGATGTGATTTTTTCCGTTTCCTCCCCTTTGGATGCTGAATA
TCTGGTTCAGAGTGCAGCCAGAAATTTTGGGATGGAAGTGACCTCATCAGATAAATCTGGTC
CCCCAAGACTTTTGAAAATGGATGAGATTGAATTTTTAAAGAGGACAACAAAATTTTTTCCT
GGCTCCACCTATAAGGTGGGGGCCTTGAGCCTGGATACCATGGAACAACATATTATGTGGAT
GAAGAATTTGGAAACCTTTCCAGAACAACTTGTTAGCTTTGAAAATGAGTTGGTGTTGCATG
GGAAAGAAATTTATGATGATTATAAAGTAGGTTTAATCCTATTTTGAATCAATGGCGAGTG
TGCATGCAGGACTATGAAGTGGCCCTGCATCGCATGCTACGCTATGTTTTTGATTAAATTGA
TTTAATTTGATTTTGATTTTGTTAGTTTTAGTTTAAGTAAGTTAGAATTAGATTATTTAAT
TTAGCTTTAAAGATTTTGATTTGATTGAATTTGGCCCACCAATC

DIABETIC MODEL

This application is a national stage application (35 U.S.C. § 371) of International application number PCT/IB02/03957, filed Aug. 21, 2002, and claims priority under 35 U.S.C. § 119 from United Kingdom application number 0120437.9, filed Aug. 22, 2001, incorporated herein in its entirety by reference.

TECHNICAL FIELD OF INVENTION

The present invention relates to a method for obtaining an animal model for diabetes. The present invention also relates to the uses of the animal model for screening for or testing compounds which affect diabetic symptoms. The present invention also relates to an assay for determining an individual's susceptibility to developing diabetes.

BACKGROUND OF THE INVENTION

Diabetes is a disease in which the body does not produce or use insulin correctly. Insulin is a hormone that is required to convert sugar, starches and other food into energy needed for daily life. Insulin is produced by the beta cells in the islets of Langerhans in the pancreas. Partial or total loss of these cells will result in partial or total loss of insulin production.

There are two major types of diabetes.

Type 1 diabetes is an autoimmune disease in which the body actually fails to produce any insulin. Type 1 disease most often occurs in children and young adults but can develop at any age. Type 1 diabetes is characterized by total loss of beta cells so that the patient requires insulin by injection. Type 1 diabetes accounts for 10-15% of all diabetes. Type 1 diabetes is strongly associated with auto-antibodies and this association has become part of the definition/classification of type 1 diabetes. Type 1 diabetes is discussed in greater detail below.

Type 2 diabetes is a metabolic disorder resulting from the body's inability to make enough, or properly use, insulin. It is the most common form of the disease. Type 2 diabetes accounts for 85-90% of diabetes.

The definitions of type 1 and 2 diabetes, however, are changing slowly. Auto-antibodies are found in type 2 diabetes patients and type 2 diabetes is found in increasing numbers in children. As a result, the traditional view of type 1 and 2 diabetes as two different diseases both resulting in increased blood glucose levels is shifting to the view that there is a large grey zone with patients in between the two extremes. This view is important when evaluating the usefulness of different animal models.

Both genetic and environmental factors are believed to be involved in the development of type 1 (insulin dependent) diabetes (for reviews see Leslie et al., Diabetologia, 42, 3-14, 1999; and Schranz et al., Diab. Metab. Rev., 14, 3-29, 1998). The HLA Class II region is the strongest genetic component, but other genes and loci have been implicated as contributing to a genetic predisposition to the disease (reviewed in Schranz et al., 1998 (supra)). Monozygotic twin studies show only 20-30% concordance of type 1 diabetes indicating a significant contribution of environmental factors (Kyvik et al., BMJ, 311, 913-7, 1995). The role of environmental factors is also supported by the fact that more than 85% of new onset patients do not have a first degree relative with the disease (Dahlquist et al., Diabetologia, 32, 2-6, 1989).

Worldwide, there is a large variation in the incidence of type 1 diabetes, ranging from more than 40 patients per 100,000 in Finland to 1-2 cases per 100,000 in Japan (Onkamo et al., Diabetologia, 42, 1395-403, 1999). Seasonal variation in incidence rate, together with serological studies, have suggested viral infections as a major environmental risk factor for type 1 diabetes (for reviews see Jun et al., Diabetologia, 44, 271-285, 2001; Rayfield et al., Diab./Metab. Rev., 3, 925-57, 1987; and Vaarala et al., Diabetes Nutr. Metab., 12., 75-85, 1999). Congenital rubella virus infection (Menser et al., Lancet, i, 57-60, 1978) or different members in the enterovirus genus are most often implicated as an etiologic agents in diabetes development (Yoon, Do Viruses Play a Role in the Development of Insulin-dependent Diabetes?, 1991; Vaarala et al., 1999, (supra)). Signs of enterovirus infection during pregnancy (Dahlquist et al., Diabetologia, 32, 2-6, 1989; and Hyoty et al, Diabetes, 44, 652-657, 1995) and in some infants who developed islet cell autoantibodies and later type 1 diabetes (Lonnrot et al., Diabetes, 49, 1314-8, 2000) further supports this hypothesis. Both Coxsackie B and rota virus contain peptide sequences also found in the islet autoantigens glutamate decarboxylase (GAD65) (Kaufman et al., J. Clin. Invest., 89, 283, 292, 1992), the tyrosine-phosphatase like protein IA-2 (Honeyman et al., Diabetes, 49, 1319-1324, 2000) or proinsulin (Rudy et al., Mol. Med., 1, 625-33, 1995) suggesting that T lymphocytes recognizing viral antigens may potentially contribute to islet autoimmunity by cross-reactivity or molecular mimicry. Indeed, cross-reactive GAD65 and rubella virus peptides were recognized by T cells in type 1 diabetes patients (Ou et al., Diabetologia, 43, 750-62, 2000). Since T cell tests that predict type 1 diabetes are not yet available, standardized tests for GAD65, IA-2 or insulin autoantibodies are useful markers to predict type 1 diabetes (for a review see Gottleib et al., Arum. Rev. Med., 49, 391-405, 1998). Rota virus seroconversion was reported to be associated with increases in autoantibodies to GAD65, IA-2, and insulin suggesting that this virus infection may trigger or exacerbate islet autoimmunity in genetically susceptible children (Honeyman et al., 2000 (supra)). Coxsackie virus-induced diabetes in mice was also associated with the development of GAD antibodies (Gerling et al., Autoimmunity, 6 49-56,1991). It is still controversial, however, whether viruses cause beta cell destruction directly by a cytolytic infection in the islets or indirectly by initiating autoimmunity (Vreugdenhil et al., Clin. Infect. Dis., 31, 1025-31, 2000; and Kukreja et al., Cell Mol. Life Sci., 57, 534-41, 2000).

Rodents are well-known reservoirs and vectors for viruses causing disease in humans. Puumala virus causing Nephropathia Epidemica (Myhrman, Nordisk Medicinsk Tidskrift, 7, 739-794, 1934; and Niklasson et al., Lancet, 1, 1012-3, 1984) is one example of an important human pathogen carried by bank voles. It has been demonstrated that the incidence rate of human Nephropathia Epidemica correlates with the vole population density during the previous year (Niklasson et al., Am. J. Trop. Med. Hyg., 53, 134-40, 1995). More recently, statistical evidence suggests that type 1 diabetes in humans also tracks the 3- to 4-year population density cycles of the bank vole with a similar time lag (Niklasson et al., Emerg. Infect. Dis., 4, 187-93, 1998). It also was observed that a high frequency of bank voles trapped in the wild and kept in the laboratory for studies of stereotypic behavior (Schoenecker et al., Appl. Anim. Behav. Sci., 68. 349-357, 2000) develop symptoms of type 1 diabetes, i.e., polydipsia and glucosuria, at a high frequency.

Currently there are two main animal models of diabetes: the NOD (non obese diabetic) mouse and the BB (bio breeding) rat. Both models involve animals with insulin dependent diabetes. Both of the current models, however, fail to display important symptoms of human diabetes. The NOD mouse, for example, shows gender preferences that are opposite to the human disease (i.e., more females than males develop the disease), develops mild diabetes, requires a long time before developing ketoacidosis, and fails to develop autoantibodies to GAD65, 1A-2 or insulin. The disease is genetically controlled in the NOD mouse and the cleaner the animal, the higher the frequency of diabetes.

The BB rat is also no ideal. The animals have lymphopenia controlled by an autosomal mutation on chromosome 4 and the development of autoantibodies in inbred and specific pathogen free BB rats appears negligible. None of these BB rats develop diabetes in association with an infectious agent.

Thus, there is a need to develop an improved method for obtaining an animal model which displays the features of diabetes for both research and therapeutic purposes.

SUMMARY OF THE INVENTION

The invention provides an animal model for human diabetes and methods for producing it. The invention also provides methods for screening for or testing compounds which affect diabetic symptoms comprising use of the animal model. The invention further provides an assay for determining an individual's susceptibility to developing diabetes.

BRIEF DESCRIPTION OF DRAWINGS

FIG. 1 shows the histology of the pancreas in bank voles without diabetes (panels a and b as well as e and f) and with diabetes (panels c and d as well as g and h). The histology of non-diabetic bank voles demonstrates well-defined islets of Langerhans surrounded by a conspicuous and delicate capsule. Diabetic bank voles have dramatic islet cytopathology characterized by distinct vacuoles or fatty infiltration of the pancreatic islets. Hematoxylin and Eosin staining are shown in panels a-d while immunostaining for insulin and glucagon are shown in panels e-h. The immunostained sections demonstrate that the cytopathology affected only insulin positive cells, which were lost resulting in a redistribution of glucagon immunoreactive cells. Size bars are indicated in each panel.

FIG. 3 shows the histology of the pancreas in bank voles without (panels a and b) and with diabetes (panels c and d) following immunostaining with the mouse 87-012 or 145L antiserum against Ljungan virus. The binding of the mouse antiserum was revealed with red vector staining. The sections were double stained with glucagon antiserum revealed with alkaline phosphatase and tetrazolium blue. The non-diabetic voles did not show binding of mouse anti-Ljungan virus antibodies while the immunostaining against glucagon stained cells in the periphery of the islets (panel a). The islets in diabetic bank voles showed varying degree of vacuolization or fatty infiltration of the pancreatic islets (panels b, c and d). The edges of these lesions are stained indicating the presence of Ljungan virus antigen. The glucagon immunostaining showed redistribution of cells that became more pronounced the greater the lesions.

FIG. 7 shows the nucleotide sequence of Ljungan virus 87-012.

FIG. 8 shows the nucleotide sequence of Ljungan virus 145SL.

FIG. 9 shows the nucleotide sequence of Ljungan virus 174F.

DETAILED DESCRIPTION OF THE INVENTION

Figure 2:
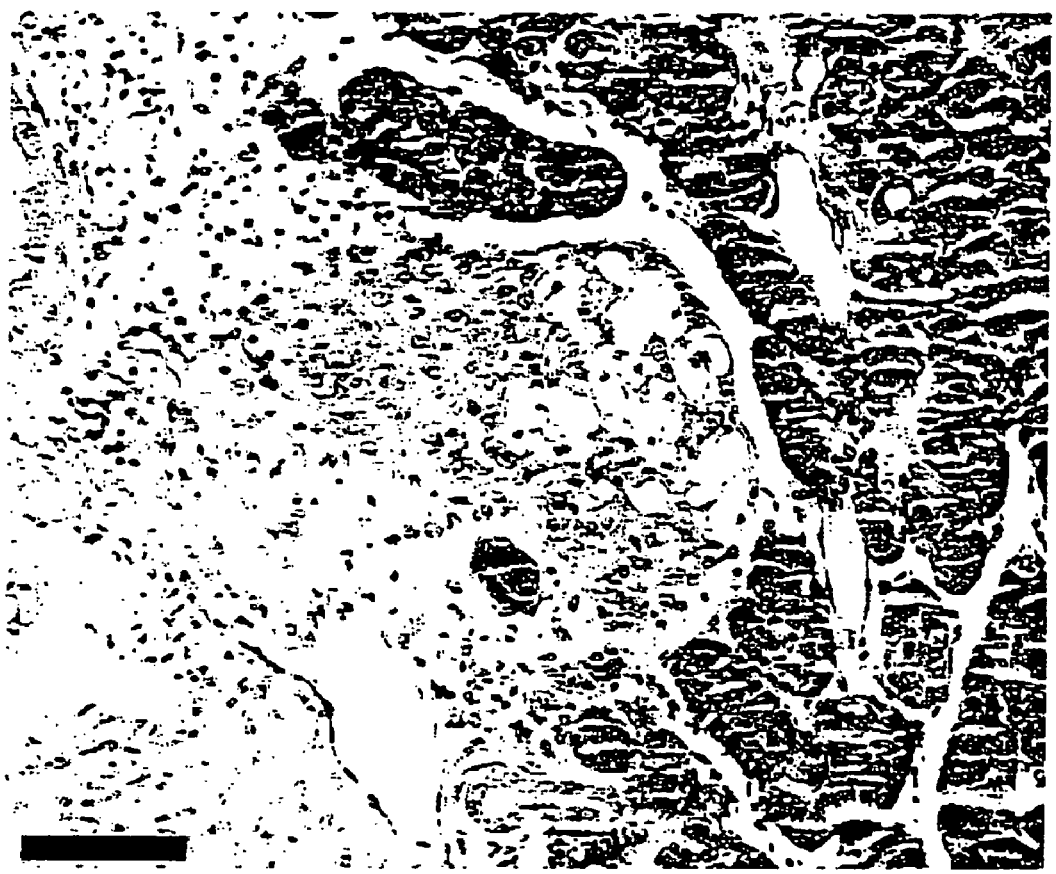
FIG. 2 shows the histology of the pancreas of a diabetic bank vole demonstrating islet infiltration of mononuclear cells following Hematoxylin and Eosin staining.

According to a first embodiment of the present invention, there is provided a method for obtaining an animal model for human diabetes, comprising obtaining a mammal that has been determined to be infected with Ljungan virus.

The mammal may be any mammal including rodents such as rats, mice, hamsters, guinea pigs, rabbits, bank voles and field voles; cattle such as cows; cats; dogs; and non-human primates. Preferably the mammal is a rodent, a cat or a dog, more preferably the mammal is a rodent, most preferably the mammal is a bank vole.

It has been found that bank voles having type 1 diabetes are all infected with Ljungan virus and that the presence of Ljungan virus causes or at least contributes to the development of type 1 diabetes.

The term "Ljungan virus" as used herein refers to any Ljungan picornavirus as defined in International PCT patent application WO 98/11133, the disclosure of which is incorporated herein by reference. Preferably the Ljungan virus is Ljungan virus 87-012, the nucleotide sequence of which is shown in FIG. 7; Ljungan virus 145SL, the nucleotide sequence of which is shown in FIG. 8; or Ljungan virus 174F, the nucleotide sequence of which is shown in FIG. 9.

The presence of Ljungan virus can be determined using any standard procedure including, but not limited to, virus isolation, detection of Ljungan virus antigen by ELISA or immunohistochemistry using antibody molecules having affinity for Ljungan virus or detection of Ljungan virus specific RNA sequences using PCR or by a labeled nucleic acid probe capable of specifically hybridizing to Ljungan virus nucleic acid. The presence of Ljungan virus also can be determined by detecting for the presence of Ljungan virus antibodies using a suitable test. Suitable techniques for determining the presence of Ljungan virus or anti-Ljungan virus antibodies are described in the examples below.

Use of the mammal obtained by the method according to the first embodiment of present invention as a model for human diabetes has a number of advantages over the prior art animal models of diabetes including:

- a pathology that includes total destruction of the beta cells without affecting the surrounding pancreas tissue;
- no or minor signs of inflammatory cells and only modest insulitis; and
- the presence of auto-antibodies used as markers for human type 1 diabetes (antibodies to GAD 65, IA-2 and insulin) in most bank voles obtained by the method according to the first embodiment of the present invention.

The fact that the mammal obtained using the method according to the first embodiment of the present invention has features that mimic the human disease means that it closely represents the human disease and is therefore a particularly useful model of diabetes.

Preferably, the method according to the first embodiment of the present invention also comprises determining whether the mammal has high blood glucose levels that can be reduced by insulin and signs of ketoacidosis.

Preferably, the mammal is a bank vole. The bank vole may be any species of bank vole. Preferably the bank vole is *Clethrionomys glareolus*. The mammal can be male or female. The bank vole may be obtained from the wild or may be the progeny of a bank vole obtained from the wild. It is preferred that the bank vole obtained from the wild is obtained from Denmark, Sweden or Finland. Alternatively, the bank vole may be a laboratory bred bank vole.

The term "diabetes" as used herein means type 1 or type 2 diabetes or diabetes having a combination of symptoms of both type 1 and type 2 diabetes. The type of diabetes developed by the mammal will depend on the type of mammal. For example bank voles infected with Ljungan virus develop type 1 diabetes, whereas cats and dogs can develop type 1 or type 2 diabetes or diabetes having a combination of symptoms of both type 1 and type 2 diabetes. It is currently believed that diabetes in humans is not always type 1 or type 2 diabetes but that diabetes can fall somewhere between the two defined types wherein the individual has some symptoms of both type 1 and type 2 diabetes. The term "diabetes" as used herein refers to diabetes characterized by high blood glucose levels that can be reduced by insulin and signs of ketoacidosis. The presence of auto-antibodies to at least one of GAD65, IA-2 and insulin is an additionally preferred characteristic of type 1 diabetes according to the present invention. Additional features of diabetes such as hyperlipidemia, slowly progressive increase of hyperglycemia and variable glucosuria as well as symptoms of hyperphagia and obesity also may be present in addition to the characteristics of type 1 diabetes defined above in accordance with the situation in humans.

The term "high blood glucose levels" as used herein means blood glucose levels that are at least 1.5 times as high, more preferably at least 3 times as high and most preferably at least 5 times as high as the mean level of blood glucose found in the corresponding non-diabetic mammals. Non-diabetic mammals are mammals that do not show any symptoms of diabetes such as increased glucosuria. It is particularly preferred that a high blood glucose level is at least 150 mg/dl, more preferably at least 200 mg/dl.

The term "reduced by insulin" as used herein means that the high blood glucose levels can be reduced by the addition of insulin. Preferably the blood glucose levels can be reduced by about 30%, more preferably 60% and most preferably to approximately the level of a non-diabetic mammals by the addition of insulin. As those skilled in the art will appreciate, the reduction in blood glucose levels will vary depending on the amount of insulin given to the mammal.

Signs of ketoacidosis include nausea, vomiting, stomach pain, deep and rapid breathing, flushed face, dry skin and mouth, fruity breath odor, rapid and weak pulse, low blood pressure. Ketoacidosis can be determined by the measurement of keton bodies in the blood or in plasma or serum.

The method according to the first embodiment of the present invention preferably additionally comprises modulating the immune system of the mammal to facilitate the development of diabetes. The modulation can be by suppressing or enhancing the immune system. The immune system of the mammal can be modulated by any method including administrating immunosuppressing or immunostimulating agents, altering the diet of the mammal or subjecting the mammal to stress. Preferably the immune system of the mammal is modulated by subjecting the mammal to stress. The mammal can be subjected to any form of stress that affects the immune system of the mammal including keeping the mammal in a cage. In embodiments in which the mammal is a bank vole, it preferably is kept in a cage for at least 2 months, more preferably at least 3 months. Preferably the mammal is kept isolated in its own cage.

The present invention also provides the use a mammal infected with Ljungan virus as a model of diabetes.

The mammal used as a model of diabetes is preferably obtained by the method according to the first embodiment of the present invention.

The mammal can be used as a model of diabetes in order to investigate the development and etiology of diabetes. The mammal can also be used to test candidate compounds for their effects on symptoms of diabetes. In particular, a candidate compound can be administered to the mammal and the effects of the compound on symptoms of diabetes, such as blood glucose levels, signs of ketoacidosis and glucosuria can be measured.

The mammal can also be used to screen for compounds having an effect on the development of diabetes. Preferably the mammal is used to screen for compounds that prevent the development of, or reduce the symptoms of, diabetes.

The present invention also relates to the use of compounds identified in the above-described screening in the manufacture of a composition for treating and/or preventing diabetes.

The present invention also relates to the use of cells obtained from mammals obtained by the method according to the first embodiment of the present invention. The cells can be used in a variety of in vitro assays which are well known to those skilled in the art.

In a second embodiment of the present invention there is provided a method for producing diabetes in a mammal comprising infecting the mammal with a Ljungan virus.

It has been found that mammals infected with Ljungan virus develop diabetes. The mammal infected with Ljungan virus can be used as a model of diabetes whether or not symptoms of diabetes can be detected.

The mammal can be infected using any standard technique, including, but not limited to, parenteral routes such as intravenous injection and intraperitoneal injection. Methods for determining the necessary viral dose leading to the development of diabetes can be easily determined by those skilled in the art. In making such a determination, a number of factors are considered including the species of mammal, the rate of viral replication, the route of infection, the age and sex of the mammal. Preferably about 1,000 infection units are given to the mammal.

The mammal infected with Ljungan virus may develop type 1 or type 2 diabetes or diabetes having a combination of symptoms of both type 1 and type 2 diabetes.

The method according to the second embodiment of the present invention preferably additionally comprises modulating the immune system of the mammal as described above with respect to the first embodiment of the present invention. Preferably the immune system of the mammal is compromised by subjecting the mammal to stress as described above with respect to the first embodiment of the present invention subsequent to infection with the infectious agent.

By compromising the immune system of the mammal, it has been found that the animals develop diabetes more quickly. Without being bound to any one theory, it is believed that the Ljungan virus can replicate at a faster rate leading to the development of diabetes in a shorter period of time in immune-compromised animals.

The present invention also provides the use of a mammal infected with a Ljungan virus as a model of diabetes. Preferably the mammal is obtained by the method according to the second embodiment of the present invention.

The mammal infected with a Ljungan virus can be used as a model to investigate the development and etiology of diabetes. The mammal also can be used to test candidate compounds for their effects on diabetes. In particular, a candidate compound can be administered to a mammal infected with a Ljungan virus and the effects of the compound on symptoms of diabetes, such as blood glucose levels, signs of ketoacidosis, glucosuria, hyperlipidemia, a slowly progressive increase in hyperglycemia, symptoms of hyperphagia, obesity and insulin resistance, can be measured.

The mammal infected with a Ljungan virus can also be used to screen for compounds having an effect on the development of diabetes. Preferably the mammal is used to screen for compounds which prevent the development of, or reduce the symptoms of, diabetes.

The present invention also provides an assay for determining an individual's susceptibility to developing diabetes comprising analyzing a sample from the individual in order to determine if the individual is infected with a Ljungan virus, wherein infection with a Ljungan virus indicates a greater susceptibility to developing diabetes.

It has been found that children with an increased level of antibodies against Ljungan virus have type 1 diabetes (i.e., serologically positive for Ljungan virus infection). We have determined that a population of children with diabetes has a much higher frequency of being serologically positive for Ljungan virus than in a population of healthy control children.

The presence of Ljungan virus can be determined using any standard procedure including immunohistochemistry using antibody molecules having affinity for Ljungan virus or by using a labeled nucleic acid probe capable of specifically hybridizing to Ljungan virus nucleic acid. Alternatively the presence of Ljungan virus can be determined by detecting the presence of anti-Ljungan virus antibodies using a suitable test. Suitable techniques for determining the presence of Ljungan virus or anti-Ljungan virus antibodies are described in the examples below.

The present invention also provides a method of treating an individual who has developed diabetes or is susceptible to developing diabetes comprising administering an effective amount of a compound which prevents or reduces Ljungan virus-induced diabetes.

Compounds which prevent or reduce the effects of Ljungan virus include antibody molecules having affinity for Ljungan virus or any other anti-viral agents. Methods for producing suitable antibody molecules are well know to those skilled in the art.

The present invention also provides a method of vaccinating an individual against a Ljungan virus infection, thereby preventing, at least in part, the individual developing diabetes.

Vaccines of the invention may comprise any antigenic portion of the Ljungan virus (e.g. a protein displayed on the surface of the virus) or by using an attenuated form of the Ljungan virus. Methods for producing vaccines based on antigenic components or attenuated forms of the virus are well known to those skilled in the art and are described in a variety of literature know to those skilled in the art (see Textbook Field's Virology by David M. Knipe et al).

In another aspect, the invention includes nucleic acid molecules isolated from Ljungan viruses or any portion thereof. In some embodiments, the nucleic acid is the one shown in any one of FIG. 7, 8 or 9 or any portion thereof.

The invention further comprises a nucleic acid molecule encoding a Ljungan virus polypeptide, or fragments thereof. In some embodiments, the nucleic acid is operably linked to one or more expression control sequences. In some embodiments, the nucleic acid molecule or fragment is incorporated into a vector. In some embodiments, the vector is an expression vector.

The invention also provides host cells comprising a nucleic acid or vector of the invention. The host cell can be prokaryotic or eukaryotic. The choice of host cells for expressing a Ljungan virus polypeptide is well-known in the art.

The invention further provides methods for producing a Ljungan virus polypeptide or fragment thereof comprising culturing host cells of the invention under conditions suitable for the expression of the polypeptide and recovering the polypeptide.

The invention further comprises a vaccine comprising at least one Ljungan virus polypeptide or an immunogenic fragment thereof. In some embodiments, the vaccine comprises a plurality of Ljungan virus polypeptides or immunogenic fragments thereof. The Ljungan virus polypeptides can be from the same or different strains of Ljungan virus. Vaccines comprising polypeptides from different strains are useful to prevent or inhibit infection by a broader range of Ljungan virus in conditions caused by Ljungan virus infection, including diabetes.

In some embodiments, Ljungan virus polypeptides are a component of a multivalent vaccine that comprises one or more components from other pathogens, including human pathogens.

In some embodiments, a vaccine of the invention comprises an adjuvant. Methods for selecting an adjuvant for use in the vaccine are well-known to those of skill in the art.

The invention further provides an antibody that specifically binds Ljungan virus or a Ljungan virus polypeptide. In some embodiments, the antibody specifically binds one or more of the Ljungan virus polypeptides shown in FIGS. 7-9.

EXAMPLES

In order that this invention may be better understood, the following examples are set forth. These examples are for the purposes of illustration only and are not to be construed as limiting the scope of the invention in any manner.

Materials and Methods

Wild caught bank voles (Group A). Group A bank voles represent 101 animals from a single trapping session. These bank voles were tested at the trap for glucosuria and then euthanized. Heart-blood samples for blood glucose, ketosis, lipids and antibody analyses were taken immediately after the voles were killed. Blood samples were either immediately analyzed for blood glucose and ketones or centrifuged for 25 minutes at 1,000×g and plasma stored at −30° C. Pancreas was dissected and fixed in 4% paraformaldehyde followed by ethanol before being embedded in paraffin.

Voles caught in the wild and kept in the laboratory (Group B). In two other trapping sessions, 163 voles were caught and transferred to the laboratory as previously described (Schoenecker et al., Appl. Anim. Behav. Sci, 68, 339-347, 2000; Schoenecker et al., Appl. Anim. Behav. Sci., 68. 349-357, 2000). The animals were housed individually in small barren cages of transparent plastic (13.5×16.0×22.5 cm) under conditions of minimum extraneous disturbance and with a twelve-hour light regime (8.00-20.00 h). The cages were supplied with a woodcutting bed, and food (standard rat chow) and water were available ad libitum. Cage cleaning and body weight measurements were performed once every week. A portion of grain mixture was given when the cages were cleaned. Diabetes development was followed by measurements of water intake, glucosuria, and blood glucose and ketonemia determined after bleeding from the retro orbital plexus. Polydipsic voles were characterized by >21 ml/day water intake compared with non-polydipsic voles for which daily intake did not exceed 12 ml.

Histological analysis and immunocyto-chemistry. Standard hematoxylin and eosin staining was carried out on samples fixed in 4% paraformaldehyde, embedded in paraffin, cut into 5 micron sections, and affixed to slides. Sections were deparaffinized, rehydrated, and stained for three minutes in Gill's hematoxylin and for one minute in Eosin Y. Stained sections were dehydrated and mounted.

In the immunohistochemistry tests, pancreas fixed in 4% paraformaldehyde and embedded in paraffin were cut into 5 micron thick sections, affixed to slides, deparaffinized and rehydrated. The sections were blocked for 30 min at RT in PBS containing 0.05% Tween 20 (Sigma, St. Louis, Mo.), 1% BSA (Sigma), 2% normal horse (in the case of staining for Ljungan virus antisera) or 2% normal goat (in the case of insulin or glucagon staining) serum (Vector Laboratories, Burlingame, Calif.), and 4 drops/ml Avidin solution (Avidin/Biotin blocking kit, Vector Laboratories). The primary antibody was diluted in PBS with 0.05% Tween 20, 1% BSA, 2% normal serum, and 4 drops/ml Biotin solution (from Avidin/Biotin blocking kit, Vector Labs) to 1:100 (guinea pig anti-insulin and rabbit anti-glucagon, Zymed Laboratories, S. San Francisco, Calif.) or 1:500 (mouse Ljungan virus antiserum). Slides were exposed to the primary antibody solution for 60 minutes at room temperature or overnight at 4° C. Slides were then washed in PBS, incubated for 30 minutes at room temperature with a biotinylated secondary antibody (goat anti-rabbit IgG, goat anti-guinea pig IgG, or horse anti-mouse IgG (Vector Labs) diluted 1:500 in PBS, and washed again. The slides were next incubated for 30 minutes at room temperature in alkaline phosphatase streptavidin conjugate (Vector Labs) at a 1:200 dilution, washed in PBS, and reacted with the Vector Red or Vector BCIP/NBT alkaline phosphatase substrate kit. Finally, slides were counter stained with methyl green, dehydrated, and mounted. All slides were coded and scored independently by two readers.

Immunfluorescence assay for Ljungan virus antibodies. Sera from children with type 1 diabetes and controls were tested for presence of antibodies to Ljungan virus using an indirect immunofluorescence test (IFT). A previously described IFT protocol (Niklasson et al., J. Infect. Dis., 155, 369-76, 1987) was used to test antibody titers. Briefly, spot slides were prepared by incubating virus in Green Monkey Kidney cells for 8-10 days. At signs of discrete cytopathic effects (CPE), cells were removed from the flask with a rubber policeman and applied onto microscope slides, air dried, fixed in cold (4° C.) acetone and stored at −70° C. until used. The titer was determined after incubating the serum, diluted in PBS, on the slides at 37° C. for 1 h in a moist chamber and bound antibodies were detected by incubating FITC-conjugated goat anti-human IgG (Sigma, St Louis, Mo.) for 1 h at 37° C. Patient and control sera was first tested at a 1:8 dilution using three Ljungan virus isolates (87-012, 145SL, 174F). Any sera scoring positive for any of the three isolates were titrated again using all three isolates separately. Patients and controls positive to one or several isolates at a titer of 32 or higher was considered positive.

Radioligand binding assays for GAD65 and IA-2 antibodies. GAD65 and IA-2 were analyzed as described (Grubin et al., Diabetologia, 37, 344-350, 1994; Hampe et al., J. Clin. Endocrinol. Metab., 85, 4671-9, 2000; Vandewalle et al., Diabetes Care, 20, 1547-1552, 1997). GAD65 and IA-2 antibody levels were expressed in U/ml for GAD65 and IA-2 antibodies using the WHO/JDF standard (Mire-Sluis et al., Diabetologia, 43, 1282-1292, 2000).

Insulin autoantibodies (IAA). IAA were measured using a method for small plasma/serum samples (Williams et al., Journal of Autoimmunity, 10, 473-478, 1997). An in-house serum sample was used as the standard to express the data in arbitrary U/ml. Recombinant human insulin (Novo Nordisk, Copenhagen, Denmark) was used to determine IAA specificity as described (Williams et al., (supra), 1997).

Radioligand binding assay for Ljungan virus antibodies. We used the Ljungan virus cDNA (unpublished observation) in the coupled in vitro transcription translation assay as described for GAD65 (Grubin et al., (supra), 1994; Hampe et al., (supra), 2000). The Ljungan virus cDNA was translated into multiple components which were immunoprecipitated with Ljungan virus mouse and guinea-pig antisera (data not shown) as well as from serum for both non-diabetic and diabetic bank voles and new onset type 1 diabetic patients.

The human 591 GAD65-positive serum (Mire-Sluis et al., (supra), 2000) showed high binding and was used as an in-house standard to express antibody binding levels in arbitrary U/ml.

Competition experiments. Competition in binding between radioactive and cold antigens was carried out at half maximal binding of either the Ljungan virus 87-012 mouse antiserum or the 591 human standard serum found to be positive for antibodies against both Ljungan virus in vitro translated antigens and GAD65 (Mire-Sluis et al., (supra), 2000). Competition for binding of $^{35}$S-labeled Ljungan virus in vitro translated antigens was carried out with different concentrations of unlabeled Ljungan virus in vitro translated antigens, recombinant human GAD65 (DiamydAB, Stockholm, Sweden) or human proinsulin (Elli Lilly Company, Indianapolis, Ind.).

Type 1 diabetes patients and controls. A total of 53 children with a median age of 10.1 years (range 2.3-16.4 years of age) were diagnosed with type 1 diabetes at the St Göran Hospital and Astid Lindgren's Children's Hospital between 1992 and 1995. Within two days of diagnosis, blood samples were drawn for antibody analysis. Healthy children (7 boys, median age 12.6 (7.8-16.8 years and 10 girls, median age 13.5 (6.7-16.6 years ) were recruited from school classes in central Stockholm and children to personnel at the hospital. All children were previously healthy and without present medication. The Ethics Committee at the Karolinska Institute, Stockholm, Sweden, approved the study.

Bioinformatics. To identify regions of high local homology between the virus polyprotein and known diabetes autoantigens, we created a local database of GAD65, IA-2 and insulin sequences and ran stand alone BLAST using software from the NCBI (Altschul et al., Nucleic Acids Res., 25, 3389-402, 1997). Alignments were compiled manually to align regions of similarity onto the Ljungan protein sequence using CLUSTALW to determine similarity between non-homologous residues.

Statistics. The frequency of diabetes in the different groups was analyzed by Fischer exact test or Chi Square tests. Non-parametric tests were used to analyze differences in levels between groups. Spearmans Rank Correlation was used to examine possible correlation between different parameters.

Example 1

Obtaining Bank Voles having Type 1 Diabetes

Development of Diabetes in Trapped Bank Voles

Bank voles were trapped from May to November in a forest habitat on the island of Zealand, Denmark. In different continuous trapping sessions of 30 days duration, 100 traditional live traps were set and inspected twice a day. Two groups of bank voles were analyzed for diabetes and pancreas histology in addition to type 1 diabetes associated autoantibodies against insulin (Williams et al., (supra), 1997), GAD65 (Grubin et al, (supra), 1994), and IA-2 (Lan et al., DNA and Cell Biology, 13, 505-514, 1994) also known as ICA512 (Rabin et al., J. Immunol, 152, 3183-3187,1994) as well as antibodies against Ljungan virus (Niklasson et al., Virology, 255, 86-93, 1999). Group A bank voles represents 101 trapped bank voles that were euthanized in the forest for immediate examination of blood glucose, glucosuria, body weight, pancreas histology and antibodies. Group B represents 67 bank voles that were trapped and kept in the laboratory for one month as previously described (Schoenecker et al., Appl. Anim. Behav. Sci., 68, 349-357, 2000). An additional group of 54 animals were examined in Stockholm for insulin sensitivity and pancreas histology before and after diabetes development.

The data in Table 1 shows the occurrence of diabetes in the two groups of bank voles. In the Group A bank voles (n=101), four female animals were found positive for glucosuria and blood glucose values of 215, 302, 313 and 340 mg/dl, respectively, In the remaining bank voles, the mean blood glucose±S.D. was normally distributed at 101±28 mg/dl. The body weight of the trapped voles from group A ranged from 8.5-28.4 g, the mean value±S.D. was 19±5 g. Occasional hyperglycemic and glucosuric bank voles may therefore be trapped in the wild. Whether these four animals had stress-induced hyperglycemia or overt diabetes remains to be established. These results in the Group A bank voles differ markedly from the 67 Group B bank voles that were trapped and kept in standard laboratory mouse cages for one month before they were tested for diabetes. We observed that 22/67 (33%) of these Group B bank voles had a blood glucose above 200 mg/dl, the range being 211-540 mg/dl. As many as 18/22 (82%) had ketones and were polydipsic. Gender differences are common in both humans (Harris, Diabetes in America, (ed. Harris, M. I.) (National Institutes of Health, Bethesda, 1995) and in animal models of diabetes as well as in captured wild rodents that develop non-insulin dependent diabetes when fed laboratory chow (for a review see (Shafrir et al., Diabetes Metab. Rev., 8, 179-208, 1992). The bank voles we captured were also fed laboratory chow but they were not only glucosuric and hyperglycemic but also positive for ketonuria, ketonemia and hyperlipidemia, all suggestive of type 1 diabetes (data not shown). An insulin sensitivity test (Actrapid, Novo Nordisk, Copenhagen, Denmark) was also carried out in 16 randomly selected Stockholm bank voles to exclude diabetes due to insulin resistance. At 60 minutes following insulin, four animals with blood glucose levels above 200 mg/dl experienced 30% decrease in blood glucose, four animals with blood glucose at 120-200 mg/dl showed 60% decrease while eight animals with blood glucose <120 mg/dl showed a 40% decrease in blood glucose. These data indicate that bank voles with varying blood glucose levels are insulin sensitive. We therefore next examined the pancreas histology in non-diabetic and diabetic bank voles to test if the classification of type 1 diabetes was supported by a loss of beta cells.

TABLE 1

The frequency of diabetes in wild caught bank voles and in bank voles kept in the laboratory.

| | Group of bank voles | |
| --- | --- | --- |
| | A. Analyzed at trap | B. Trapped and captive |
| N | 101 | 67 |
| M/F ratio | 42/59 | 29/38 |
| Blood glucose (mg/dl) | | |
| Non-diabetic | 101 ± 27 | 86 ± 24 |
| Diabetic | 293 ± 54 | 346 ± 88 |
| Diabetes n (%) | 4 (4%) | 22 (33%) |
| M/F ratio | 0/4 | 14/8 |

Mean values ± S.D are shown.

Bank Voles Develop Type 1 Diabetes Because of a Specific Loss of Beta Cells

The pancreas of all 101 Group A bank voles showed normal islets as did those of non-diabetic Group B bank voles (FIG. 1). The four hyperglycemic Group A bank voles had no appreciable islet lesions. Immunostaining with insulin and glucagon antibodies showed a normal islet cell distribution with beta cells located in the center surrounded by glucagon-positive cells (FIGS. 1a and 1b). In dramatic contrast, Group B bank voles with diabetes had an almost complete loss of centrally located insulin-positive cells that were replaced by prominent vacuolization or fatty infiltration (FIGS. 1c and 1d). Islets with infiltrating mononuclear cells were occasionally observed (FIG. 2) but insulitis was conspicuously absent in the majority of the bank voles. The beta cell destruction was unique to bank voles with diabetes and indicate that the animal should be classified as having type 1 diabetes.

In order to evaluate whether the Ljungan virus was associated with the islet beta cell lesion we next immunostained the pancreas sections with high titer mouse antisera against Ljungan virus (Niklasson et al., (supra), 1999). We used antisera to two distinct Ljungan virus isolates, 87-012 and 145SL and, as controls, eight different antisera prepared with the same procedure against Rift Valley Fever virus, Ockelbo virus, Langat virus and Sindbis virus. Both the 87-012 and the 145SL Ljungan virus antisera at dilution of 1:4000 or higher immunostained islets in diabetic but not in non-diabetic bank voles (FIG. 3) visualizing the presence of Ljungan virus antigen in affected islets. None of the control sera showed immunostaining at a dilution of 1:500 or higher. Furthermore, an analysis of Stockholm bank voles euthanized with variable blood glucose levels after 2-3 months of captivity revealed that the severity of beta cell loss was gradual (FIG. 3 panel b, c and d). Also in these apparently early lesions, a mononuclear cell infiltration was conspicuously absent. Without being bound to any one theory, it is submitted that the beta cell-specific destruction in association with immunoreactive virus antigen suggests that the Ljungan virus might have had a lytic effect on the beta cells, perhaps accelerated by the stress of bringing the bank voles into captivity. Although mononuclear cell infiltration was not a prominent feature of the beta cell destruction it cannot be excluded that Ljungan virus beta cell lysis results in autoantigen presentation that takes place in lymph nodes draining the pancreas or by antigen presenting cells in or around the islets. We therefore next examined the possibility that the development of diabetes was associated with autoantibodies to the islet autoantigens GAD65, IA-2 or insulin. Autoantibodies to these autoantigens predict type 1 diabetes in humans (reviewed in Schranz et al., (supra), 1998 and Leslie et al., (supra), 1999) but not in the NOD mouse or BB rat models of type 1 diabetes (Bach et al., Endocrine Rev., 15, 516-542, 1994). The possible presence of autoantibodies to these autoantigens would further support the hypothesis that the bank voles developed type 1 diabetes.

Bank Vole Diabetes is Associated with Autoantibodies to GAD65 and IA-2

Figure 4:
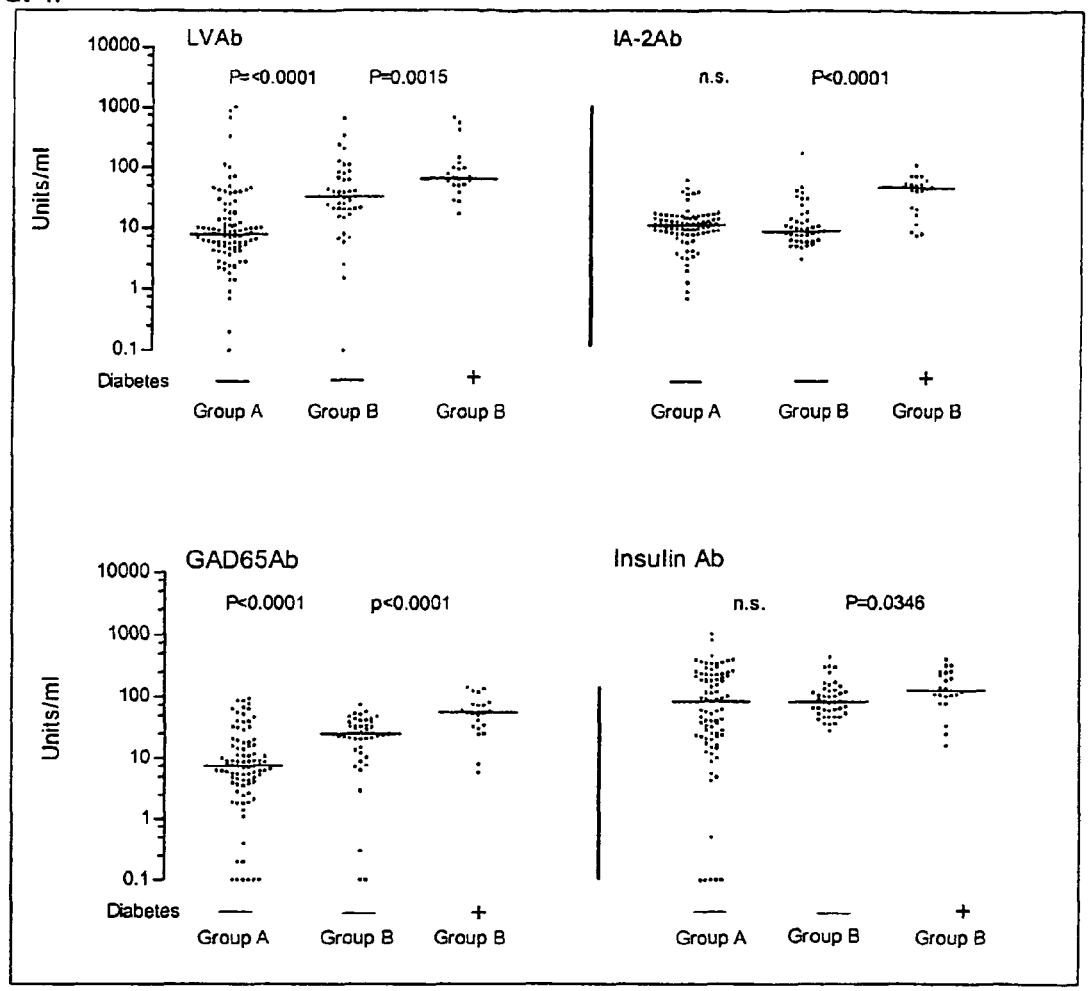
FIG. 4 shows that the bank voles have autoantibodies against islet cell autoantigens and against Ljungan virus in vitro translated antigens. Autoantibodies to GAD65 (panel a), IA-2 (panel b), insulin (panel c) as well as Ljungan virus in vitro translated antigens are shown as in-house relative Units on a log scale (wherein a 1/25 dilution of standard serum is equal to 100 units/ml). Group A animals were caught and bled in the wild and only 4% had diabetes. Group B bank voles were captive and 33% of the animals shown had diabetes. The levels of GAD65 ($p<0.0001$), IA-2 ($p<0.0001$) and insulin ($p<0.03$) autoantibodies were increased in Group B compared to Group A bank voles. The autoantibody levels of both GAD65 and IA-2 were higher in diabetic as compared to non-diabetic Group B bank voles as indicated in the Figure. The data in panel d demonstrate that antibodies to Ljungan virus in vitro translated antigens were also increased in diabetic compared to non-diabetic bank voles. Data for individual bank voles are shown.

Standardized radioligand-binding assays that detect autoantibodies to GAD65 (Grubin et al., (supra), 1994; Hampe et al., (supra), 2000), IA-2 (Kawasaki et al., Diabetes, 45, 1344-9, 1996; Vandewalle et al., (supra), 1997) and insulin (Williams et al., (supra), 1997) were used to analyze serum samples from available animals of both Group A and Copenhagen group B bank voles (FIG. 4). Compared to Group A animals, GAD65 (P<0.001) but not IA-2 or insulin autoantibodies were increased non-diabetic Group B bank voles. More importantly, however, diabetic group B bank voles had higher GAD65 (P<0.001), IA-2 (P<0.001) and insulin (P<0.0346) autoantibody levels than the non-diabetic voles (FIG. 4). The increased levels of GAD65, IA-2 and insulin autoantibodies further indicates that diabetes in these bank voles should be classified as type 1 diabetes.

Since Ljungan virus antigen was demonstrated in the islets of diabetic bank voles (FIG. 3) we next determined whether antibodies to Ljungan virus antigens were associated to GAD65 and IA-2 autoantibodies. A radioligand binding assay, similar to the GAD65 and IA-2 autoantibody assays (Grubin et al., (supra), 1994) was developed with $^{35}$S-labelled virus antigens generated by coupled in vitro transcription and translation using the T7 promoter of the Ljungan virus cDNA (unpublished results). Although the Group A bank vole sera showed a wide range of antibody levels against Ljungan virus antigen (FIG. 4), the mean levels of Ljungan virus antibodies in the non-diabetic Group B bank voles were significantly increased (P<0.001). In group B bank voles, the levels of Ljungan virus antibodies were higher in diabetic than non-diabetic animals (P=0.0015). Since the diabetic Group B bank voles also showed increased levels of GAD65, IA-2 and insulin autoantibodies, we next tested if they were related to Ljungan virus antibody levels. In the diabetic Group B bank voles, antibody levels against Ljungan virus antigens correlated with levels of GAD65 (P<0.0001), IA-2 (P<0.0001) and insulin (P<0.03) autoantibodies. These associations suggest that Ljungan virus infection may induce an immune response that will also include beta cell autoantigens. Without being bound to any one theory, there seems to be two possibilities. The first possibility is that beta cell destruction is leading to autoantigen presentation in draining lymph nodes; the second possibility is that autoantibodies are formed due to molecular mimicry between virus and the autoantigen. The latter hypothesis was tested by comparing the predicted amino acid sequences of the Ljungan virus cDNA with those of GAD65, IA-2 and insulin.

Ljungan Virus Molecular Mimicry to Islet Autoantigens

Figure 5B:
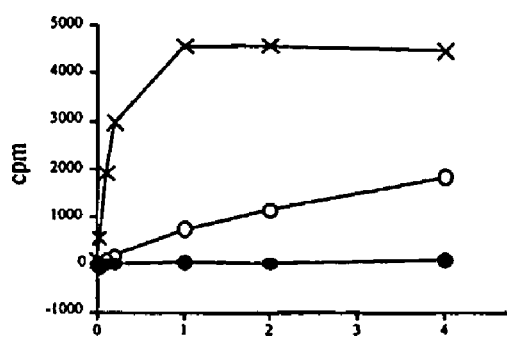
FIG. 5 shows the sequence similarities and cross-reactivity between GAD65 autoantibodies and mouse or human anti-Ljungan virus antibodies. Sequence comparisons between the predicted amino acid sequence of Ljungan virus (serotype 87-012) and type 1 diabetes associated autoantigens are shown in panel a. The data compares the 87-012 Ljungan virus sequence and regions of potential molecular mimicry to GAD65, IA-2 and insulin. Areas of homology are boxed, with identical amino acids indicated by a dot, similar amino acids are boxed, and non-similar amino acids are plain type. Antibodies against Ljungan virus raised in mice (antiserum 87-012) showed cross-reactivity with human GAD65 (panel b). Radiobinding analysis to the 87-012 antiserum showed concentration-dependent binding of $^{35}$S-labeled Ljungan virus in vitro translated antigen (x-x) and human (o-o) but not mouse (•-•) GAJD65. The competition at half maximal binding of the 87-012 antiserum between binding of $^{35}$S-labelled human GAD65 and unlabelled Ljungan virus antigen (x-x), human GAD65 (o-o) or human proinsulin (▼-▼) (panel c) demonstrates displacement by unlabelled Ljungan virus in vitro translated antigens as well as by recombinant human GAD65.
FIG. 5d. shows binding of different $^{35}$S-labeled antigens including Ljungan virus antigen (x-x), human GAD65 (o-o) or mouse GAD65 (•-•) to the type 1 diabetes human serum #591 (panel d). Human and mouse GAD65 bind equally well and there are also significant levels of antibodies detecting the Ljungan virus in vitro translated antigens. Competition at half maximal binding to human serum 591 of $^{35}$S -labelled Ljungan virus antigen and cold Ljungan virus antigen (x-x), human GAD65 (o-o) or human proinsulin (▼-▼) (panel e) showed displacement of cold Ljungan virus in vitro translated antigens but not of cold GAD65 or proinsulin. All radioactivity values in cpm are mean values±SEM for 3-5 experiments The SEM bars are within the size of the symbols unless indicated.
Figure 5C:
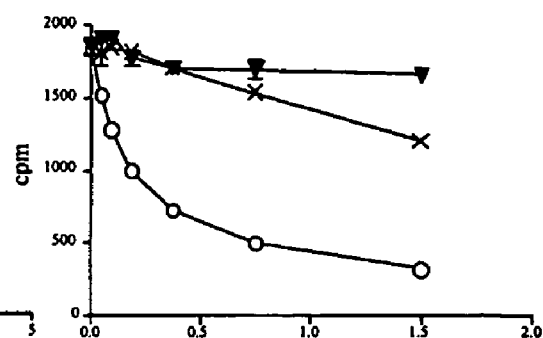
Figure 5D:
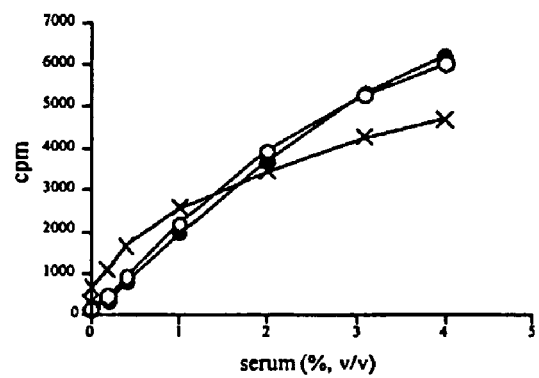
Figure 5E:
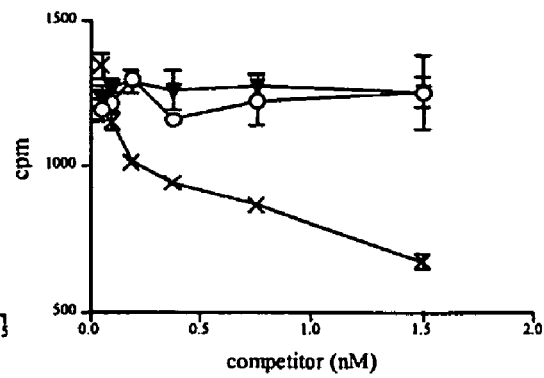

The comparison between the Ljungan virus amino acid sequence predicted from the cDNA and the GAD65, IA-2 and insulin sequences revealed several potential regions of sequence similarities (FIG. 5a). We searched 1514 picornavirus proteins in Genbank's viral taxonomy at NCBI using stand-alone BLAST and found that these homologies were exclusively found in parechoviruses (echovirus 22/23) isolates (data not shown). The regions indicated for GAD65, 237-241 and 449-452 have been implicated in the middle and C-terminal GAD65 autoantibody binding sites (Schwartz et al., J. Mol. Biol., 287, 983-999,1999). While the 561-569 is outside, the 964-976 sequence is within reported autoantibody binding sites for type 1 diabetes associated IA-2 autoantibodies (Leslie et al., (supra), 1999). The most interesting significant relationship was between the Ljungan virus antigen and the 45-54 insulin since the 45-54 homology maps to the insulin active site (Steiner et al., Diab. Care, 13, 600-609, 1990). Since antibody levels against Ljungan virus in vitro translated antigens correlated to levels of both GAD65 and IA-2 autoantibodies in the diabetic Group B bank voles and because of the significant sequence similarities (FIG. 5a), we next tested whether Ljungan virus antisera would immunoprecipitate any of the islet autoantigens. While labeled mouse GAD65 was not recognized, the mouse Ljungan virus polyclonal antiserum 87-012 (Niklasson et al., (supra), 1999) was capable of immunoprecipitating human GAD65 (FIG. 5b), indicating significant epitope specificity (Hampe et al., (supra), 2000). The Ljungan virus in vitro translated antigens immunoprecipitated by the 87-012 Ljungan virus antiserum was reciprocally displaced by both cold Ljungan virus in vitro translated antigens and human GAD65 but not by human proinsulin (FIG. 5c). The human type 1 diabetes GAD65 antibody-positive serum #591 showed concentration dependent immunoprecipitation of Ljungan virus in vitro translated antigens and both human and mouse GAD65 (FIG. 5d). Cold Ljungan virus in vitro translated antigens but not GAD65 nor proinsulin, displaced the immunoprecipitation of Ljungan virus in vitro translated antigens by the human serum (FIG. 5e). These observations support the possibility of antibody cross-reactivity due to molecular mimicry between Ljungan virus antigen and GAD65 in mice inoculated by Ljungan virus.

Example 2

Individuals Infected with Ljungan Virus are Susceptible to Developing Diabetes

We tested to see if new onset type 1 diabetes children had Ljungan virus antibodies by both standard immunofluorescence and radioligand binding assay with Ljungan virus cDNA in vitro translated antigens.

Children with Type 1 Diabetes have Ljungan Virus Antibodies

Figure 6:
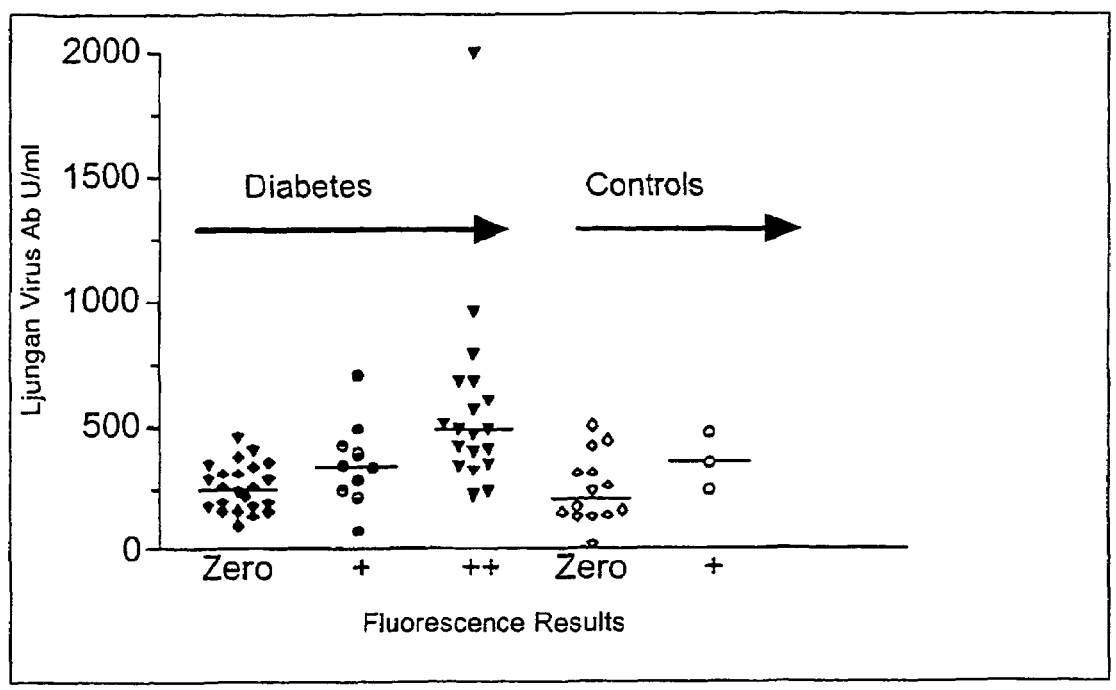
FIG. 6 shows the results of tests on sera from children with new onset type 1 diabetes indicating the presence of anti-Ljungan virus antibodies. Ljungan virus antibodies were determined in two independent tests by either indirect immunofluorescence of cells used to propagate the virus or by the radioligand binding assay with Ljungan virus in vitro translated antigens. The radioligand binding assay correlated to the indirect immunofluorescence test ($p<0.001$ at 95 confidence interval).

The commonly used indirect immunofluorescence virus antibody test was first compared to the radioligand binding assay for Ljungan virus antigen antibodies (FIG. 6). There was a significant correlation (Spearman Rank Sum correlation) between the two assays ($P<0.001$). Compared to the 17 healthy control children, the children with new onset Type 1 diabetes had increased levels of Ljungan virus antibodies scored in the immunofluorescence assay ($P<0.001$) (FIG. 6). These data indicate that children with new onset diabetes may have been exposed to Ljungan virus.

Discussion

The examples provide evidence that wild caught bank voles may develop type 1 diabetes associated with specific beta-cell destruction, insulitis and autoantibodies to GAD65 and IA-2. Our observation that it was possible to detect Ljungan virus antigen in affected pancreatic islets showing gradual destruction and end-stage fatty degeneration also indicates that this virus causes or at least contributes to the loss of beta cells. In addition, the diabetic bank voles had increased levels of antibodies to Ljungan virus cDNA in vitro translated virus antigens. The levels of these antibodies were also found to correlate to the levels of autoantibodies to both GAD65 and IA-2. These data indicate that diabetes observed in both captured bank voles and in bank voles born to captive animals represents type 1 diabetes. Although the histology of the islets in diabetic voles may be consistent with an acute lytic effect and presence of viral antigen, it cannot be excluded that beta cells may also have been lost by an ensuing T cell or antibody-mediated cellular toxicity. Also consistent with type 1 diabetes were our observations that islet beta cells were specifically lost. The prominent vacuolization or fatty infiltration seems unique to the bank voles diabetes and differ from other virus causing diabetes in rodents where insulitis is seen more often. In particular, the rare occurrence of islets infiltrated with mononuclear cells suggest that the bank vole islet lesion is less associated with insulitis compared to other diabetogenic virus (Jun et al., (supra), 2001; Rayfield et al., Diabetes, 27, 1126-1140, 1978; Vaaralae et al., (supra), 1999).

Diabetes in bank voles was first described during a study of stereotypic behavior in bank voles (Schoenecker et al., Appl. Anim. Behav. Sci., 68, 349-357, 2000) When captured in the wild, brought to the laboratory to be kept in standard laboratory mouse cages, and fed laboratory chow, bank voles developed polydipsia and glucosuria. Diabetes was detected in 4/101 Group A animals that were euthanized in the forest at the site of the trap which was different from the 22/67 bank voles kept in the laboratory. Our data suggest that the diabetes symptoms in these animals fulfill current classification criteria for autoimmune type 1 diabetes in humans (Mellitus et al., Diabetes Care, 20, 1183-1197, 1997). The diabetic bank voles sustain hyperglycemia, ketonemia, ketonuria, hyperlipidemia and weight loss, all criteria that are consistent with type 1 diabetes classification. In addition, the diabetic bank voles had increased levels of both GAD65, IA-2 and insulin autoantibodies. These autoantibodies predict type 1 diabetes in humans (Verge et al., Diabetes, 45, 926-933, 1996); Bingley et al., Diabetes Care, 22, 1796-801, 1999) and confirm the type 1 diabetes classification.

The short period of time it took for bank voles to develop diabetes after capture, and the complete islet beta cell destruction in diabetic voles associated with positive immunostaining for Ljungan virus antigen suggest that acceleration of an existing, low-level viral infection may induce disease. While the exact mechanism of such a process remains unclear, our initial studies of diabetic bank voles indicate that stress is involved in diabetes development. Early experimental stress may lead to increases in adult adrenocortical stress responses (King et al., Horm. Behav., 36, 79-85, 1999) and such stress responses may act as a stimulus of virus replication in beta cells. This speculation is supported by the observation that stress induced by swimming increased the frequency of diabetes in our wild caught bank voles (data not shown). Stress has also been implicated in human type 1 diabetes since negative life events increased the risk for childhood type 1 diabetes (Thernlund et al., Psychological Stress and the Onset of IDDM in children, 18, 1995; Hagglof et al., Diabetologia, 34, 579-83, 1991; Dahlquist et al., Diabetologia, 34, 757-762, 1991). Similar relationships could be relevant to our bank voles and therefore aid in understanding the etiology of diabetes.

It is now possible to identify other mechanisms that induce Ljungan virus-associated diabetes in bank voles and to conduct studies on intervention and protection, for example by anti-viral agents or reducing responses to stress.

It has also been found that very high Ljungan virus antigen antibody levels are observed in some of the non-diabetic Group A bank voles. This may reflect a neutralizing and protective Ljungan virus immune response with implications for future vaccination approaches.

Taken together we have demonstrated, first, that bank voles develop diabetes that fulfills the criteria for type 1 diabetes: diabetic animals showed persistent hyperglycemia associated with weight loss, ketosis and hyperlipidemia (data not shown) as well as insulin dependence associated with specific beta-cell destruction and insulitis. Second, diabetic voles had increased levels of autoantibodies to GAD65 and IA-2, and that these autoantibodies correlated to Ljungan virus antigen antibodies. Third, the association between Ljungan virus and bank vole diabetes was supported by the presence of Ljungan virus antigen detected by irnmunocytochemistry in affected diabetic bank vole islets. Fourth, there was significant molecular mimicry between the Ljungan virus polyprotein and GAD65, IA-2, and insulin islet autoantigens, illustrated by GAD65 cross reactivity of high titer mouse and guinea-pig Ljungan virus antisera. Finally, a relationship between Ljungan virus infection and human type 1 diabetes was indicated by increased levels of Ljungan virus antibodies in children with newly diagnosed type 1 diabetes.

Example 3

Data on Diabetes Mellitus in Other Mammals than Bank Voles

1. Field Voles (*Microtus agrestis*)

The field vole develops clinical diabetes with symptoms of polydipsia and polyuria identical to bank voles. Ljungan virus has been isolated from field voles with type 1 diabetes trapped in Sweden. It is likely that field voles are just as good an animal model for type 1 diabetes as the bank vole.

2. Cats

Between 1 in 50-500 will develop the disease in a lifetime. The clinical disease mimics in some animals type 1 diabetes and in some animals type 2 diabetes. Amyloid deposits localized to the islets of Langerhans are typical of type 2 diabetes mellitus. However, diabetic cats most commonly have pancreatic islet destruction associated with pancreatic amyloidosis and are insulin deficient like type 1 diabetes. The disease occurs in all ages of the cats but the majority of diabetes affect older cats (Westermark et al., PNAS USA, 84, 3881-5, 1987; Johnson et al., Veterinary Pathology, 22(5) :463-8, 1985; and Yano et al., Veterinary Pathology, 18(3) : 310-5, 1981). We have investigated the pancreas tissue of diabetic type 1 and type 2 as well as normal cats using immunohistochemistry (IHC). As in the bank voles Ljungan virus could be detected in the destroyed islets of the pancreas in the diabetic type 1 and 2 cats but not in the normal cats (Bo Niklasson unpublished observations). This is very strong evidence suggesting that Ljungan virus cause diabetes in cats.

3. Dogs

Between 1 in 50-500 will develop the disease in a lifetime. A review of the literature has shown that over half of the documented diabetic dogs are type I diabetes. However, type 2 is also common in dogs with obesity (Stogdale L. Cornell Veterinarian. 76(2) :156-74, 1986). We have investigated the pancreas tissue of diabetic type 1 and type 2 as well as normal cats using immunohistochemisty (IHC). As in the bank voles Ljungan virus could be detected in the destroyed islets of the pancreas in the diabetic type 1 and 2 dogs but not in the normal dogs (Bo Niklasson unpublished observation). This is very strong evidence suggesting that Ljungan virus caused the disease.

4. Guinea Pigs

Spontaneous diabetes mellitus in guinea pigs, parallels in many ways the syndrome known as juvenile diabetes mellitus in man: elevated blood glucose levels; reproductive dysfunction in the female; degranulation and severe cytoplasmic vacuolation of beta cells, severe fatty degeneration of acinar cells, and hyperplasia of the islets of the pancreas; and a high frequency of abnormal pancreatic secretions (Lang et al., Diabetes, 25(5) :434-43, 1976). The severity of pathologic changes in the pancreatic islets parallel, in general, the severity of the clinical symptoms. The other clinical parameters of note are elevated serum triglycerides, normal serum but elevated aortic cholesterol, and absence of ketonemia or ketonuria. Microangiopathy, another characteristic of juvenile diabetes mellitus in man was demonstrated as a significant increase in the thickness of the basal membranes in peripheral capillaries. A glomerular lesion encountered in some of the diabetic guinea pigs was shown to be similar to the glomerular sclerosis seen in human diabetics. Although a definitive etiologic agent was not identified, the disease was clearly contagious in origin.

5. Rabbits

Spontaneous diabetes mellitus has been observed in a female New Zealand white rabbit. Three groups of animals could be identified. Some animals had overt diabetes characterized by fasting hyperglycemia and depressed intravenous glucose stimulated serum insulin levels (Conaway et al., Clinical & Experimental, 30(1) :50-6, 1981). This abnormality is seen between 1 and 3 years of life. Another group of animals developed abnormal glucose disposal with normal or slight elevations in fasting serum glucose levels. Glucose stimulated insulin levels are also significantly lower in the rabbits with abnormal glucose disposal. The remaining animals exhibit no apparent abnormalities of glucose metabolism. Despite marked increases in serum and urinary glucose, only mild ketonemia was observed. The relatively late onset of diabetic symptoms, lack of obesity, severe hyperglycemia, and depressed insulin secretion without ketoacidosis make this a model with many of the characteristics of insulin responsive diabetes as seen in non-obese human adults.

6. Hamster

Chinese hamsters spontaneously develop diabetes mellitus and cardiomyopathy. The diabetic hamsters, shows body weight loss, hyperglycemia (mean fasting plasma glucose 402 mg/dl), hypoinsulinemia, hyperlipidemia and ketonemia. The diabetic hamsters showed reduced activities of cytoplasmic glycolytic key enzymes: hexokinase, pyruvate kinase and phosphofructokinase; increases in cardiac glycogen and glucose-6-phosphate contents; and a 40% decrease in cardiac ATP content, indicating decreased energy production. An accumulation of myocardial triglyceride and cholesterol was found in the diabetic hamsters (Eto et al., Diabetes Research & Clinical Practice, 3(6) :297-305, 1987).

Syrian hamsters infected with rubella virus passaged in beta-cells also develops diabetes that closely parallels the diabetes observed with congenital rubella (Rayfield et al., Diabetes, 35(11) : 1278-81, 1986). The hamsters develop hyperglycemia and hypoinsulinemia, which are sustained throughout the 15 week study period. A mononuclear infiltration of the islets, isolation of rubella virus from whole pancreas, the presence of viral antigen in beta-cells by immunofluorescence localization, and cytoplasmic islet cell antibodies (40%) are demonstrated. These data suggest that an autoimmune process and diabetes develop after rubella virus infection in neonatal hamsters. This model may uncover the precise mechanism by which rubella virus induces similar disease in humans.

All documents referred to in the above description are incorporated herein by reference.

What is claimed is:

1. A method for obtaining an animal model for human diabetes, comprising obtaining a mammal;

determining that the mammal is infected with a Ljungan virus;

modulating the immune system of the infected mammal to facilitate the development of diabetes, wherein the immune system is modulated by subjecting the infected mammal to stress; and obtaining an animal model for human diabetes, wherein the infected mammal develops diabetes.

2. The method according to claim 1, wherein the method additionally comprises determining whether the mammal has signs of ketoacidosis and high blood glucose levels that can be reduced by insulin.

3. The method according to claim 1, wherein the method additionally comprises testing for the presence of autoantibodies to at least one of GAD65, IA-2 and insulin.

4. The method according to claim 1, wherein the mammal is subjected to stress for at least about 2 months.

5. The method according to claim 4, wherein the mammal is subjected to stress by keeping it in a cage.

6. The method according to claim 1, wherein the mammal is a rodent.

7. The method according to claim 1, wherein the mammal is a bank vole.

8. The method according to claim 7, wherein the bank vole is obtained from the wild or is the progeny of a bank vole obtained from the wild.

9. The method according to claim 8, wherein the bank vole is obtained from Denmark, Sweden or Finland.

* * * * *

SEQUENCE LISTING

<160> NUMBER OF SEQ ID NOS: 12

<210> SEQ ID NO 1
<211> LENGTH: 7604
<212> TYPE: DNA
<213> ORGANISM: Ljungan virus 87-012

<400> SEQUENCE: 1

```
tttgaaaggg gtctcctggt ggggtgggta cacttctcgc tcgatgagtg ggggtgtggc      60
tcattgccca cacctggttg gttcccaggt tcatacaata accatcaata aacttttaac     120
atctaagata gtattatccc atactagact ggacgaagcc gcttggaata agtctagtct     180
tatcttgtat gtgtcctgca ctgaacttgt ttctgtctct ggagtgctct acacttcagt     240
aggggctgta cccgggcggt cccactcttc acaggaatct gcacaggtgg ctttcacctc     300
tggacagtgc attccacacc cgctccacgg tagaagatga tgtgtgtctt tgcttgtgaa     360
aagcttgtga aaatcgtgtg taggcgtagc ggctacttga gtgccagcgg attaccccta     420
gtggtaacac tagcctctgg gcccaaaagg catgtcattt gaccactcag gtacacaacc     480
ccagtgatgc acacgcttag taatggctta gtaacaaaca ttgattgatc atttgaaagc     540
tgttaggagg tttaggtatg acgggctgaa ggatgccctg aaggtaccca taggtaacct     600
taagcgacta tggatctgat caggggccca ccatgtaaca catgggtaga agtcttcgga     660
ccttgggtta aaaaacgtct aggccgcccc ccacagggat gtggggtttc ccttataacc     720
ccaatattgt ataatggctg catccaaaat gaatcccgtt ggcaacctgc tctccacagt     780
ctcctcaacc gttggatctc ttctacaaaa cccctctgtt gaagaaaagg aaatggattc     840
tgaccgtgtt gctgcctcta ctacaaccaa tgctggtaat ttggtacaag cttctgtggc     900
cccaactatg cctgtcaagc cagattttaa aaacacagat gatttcttgt ccatgagcta     960
ccgttcaaca acagccccaa ccaaccccac aaaaatggtt cacttggcac atggcacttg    1020
gacaactaat cagcacagac aggcattggt cgcatcaatt actctaccgc aggcattttg    1080
gcccaatcaa gattttccgc atgggggcag tctcgttatt ttgcagcagt gcgctgtggc    1140
tttcatattc aagtacagtt gaatgttaac atcggttctg ctggttgctt gattgccgcg    1200
tacatgccaa agacggccca tgatcatatg aacacctata cttttggttc ttacaccaac    1260
ctgccacatg ttttgatgaa tgcggcaacg acatcccagg ctgatctcta tataccctat    1320
gtttttaatc ataactatgc aagaactgat tcagatgatt taggaggcat ttacatttgg    1380
gtttggtcag ctctcacagt tccatcaggt tcacctacaa cagtggatgt gaccattttt    1440
ggttcattac tcgacttgga ttttcagtgt cctcgtcctc ctggtgcaga cacagtaatt    1500
tacacacaag ggaaaagaac tgttcgaaag accaagacat caaagttcaa atgggtcagg    1560
aataaaattg acatagctga aggtccagga gcaatgaaca tcgctaatgt tctctccaca    1620
actggtggtc aaactattgc cttggttggt gaaagagcat tctatgaccc aagaacagct    1680
ggtgctgcag tgaggtgcaa ggacctcatg gagatcgcca gaatgccaag tgtgttctta    1740
ggagagagta ctgaaccaga tggtcgaagg ggctatttca cctggtcaca tacaatctca    1800
cctgttaatt gggtttttga tgaccacatt tatttggaaa acatgcccaa tctgagatta    1860
ttctcctcct gttacaacta ttggaggggc tcctttgtta ttaaactgac agtttatgcg    1920
tcaactttca acaaaggacg cttgaggatg gcatttttcc caaacagaga aggcgcctac    1980
acacaggatg aagctcagaa cgcaatcttt gttgtgtgtg atataggctt gaataatacc    2040
```

```
tttgagatga ccatccccta cacttggggc aactggatga gaccaacaag aggaaactcc    2100
ttgggacatc tgaggattga tgtgttgaac cgtcttacat acaacagttc ttccccaaat    2160
gcagtcaact gcattcttca gattaagatg ggggatgatg caatgttcat ggtgcctacc    2220
acatctaatc tagtttggca aggtctgcac tcatggggtt cagaaatgga cttggtggac    2280
tctctcgaca atccagacga gatacaagac aatgaggaaa tacaaaccca aaatgtggag    2340
gctgcacaag gggaagaagc tgcgactgaa gttggtctta gggcaacaga aaatgatggc    2400
agtcttttcag aacaattgaa tatgagtcaa cccatgttcc tgaattttaa gaagcataaa    2460
gtcaacatct atgcagcatc ccataccaaa gttgatcata ttttttggaag agcttgggca    2520
gtgggggttt ttaacacaga aacagctgcc atacaaaaat ttgatttgca ctttccaact    2580
tctactcatg gtgcattgtc tagattttc tgcttctgga ctggagagtt aaatattcac    2640
attttgaatg tgtcaaccac aaatgccttt ttgaaagttg ctcacacatg gtttggcact    2700
gattctggaa ttgcccggac agctactttg gaatcaaatg gaacaatgat tataccacca    2760
aacgagcaaa tgacactttg tgtacccctat tattctgagg ttccattaag atgtgttaaa    2820
ggttcagaca ggaattcagc cggacttggt tctctcttca cacaggctgt gggcagaaca    2880
atctctaatc gggtacaaat cttttgtgagc ttccgctgtc ctaattttt cttcccacta    2940
cctgcgccca gggaagccac gtctcgaagc atattggaac gagtggatga agcaaatgcg    3000
gaagaacttg aagctgtctt ggaagctaga acaccagatg caccgctccg cctcaagttt    3060
aatccagaag atcctttgaa acaattgcgg gaggcggcca aggcttactt taatataatg    3120
cacagtgatg aaatggattt tgccggggggg aaattttttga accaatgtgg tgacgtggaa    3180
accaacccag gccctgacat tgagttggtc tataaaaaca gaggcttcta taagcattat    3240
ggagttagat ttggtggtca tatctaccac ttgaattcac aagacattct gtcaaccgca    3300
attacaggca gtctgacttt cattaaggaa gaagatgatg caaatgggt tcatgctatg    3360
acagcaccat tggactactt tactgaaaag tacatcaatt caatggttgg ctccaaacac    3420
atcttttccg ccacctccaa ttgtgagacc attgccagag atcttttccc agggagaaag    3480
gaaataactc agtccaaagc cttggggatt attggggtca tcttgttgtc agcctctctt    3540
cttttcattgc ttgctgtacc ctgggattat tcctcacttc aaactgttta taccaatcc    3600
attgaaggtg atgcttctgg cctcacactc ctaagtcaaa gatgcatgac ttttttttc    3660
aatacaatgt gtgaaacttt taataatgat cttgttaagt ttattattaa gattttggtg    3720
cggcttttgt gctacatcgt tctttattgc catgcaccaa atatgctgac aaccatgtgt    3780
ctgggaactc ttcttgtttt ggacattaca acttgtgaaa tcttgtctgc taacaccaaa    3840
gcactctttc aggcattggt tgatggtgat gtgaagagtc ttgtctggaa aattgctgag    3900
aatatgcaat ttgcccaatc caaggatgaa caagctgagg acatggcagc aaccttcaac    3960
tttgcctctg acatggttaa ttttgtgcca atggaacaga tgagacaaga aggctggaga    4020
gaatttaatg atgtttctat gtcctttcgg catgttgaat ggtggctgac tatgttcaaa    4080
aaggtgtaca atgttctgaa aagtatttttt gctcctagta ttgaacagaa ggctgttgat    4140
tggatagatc gcaatcaaga gtacattgcc gatgtttttgg accatgcttc caacatcatc    4200
ataaaaatga aggatccaaa agaacaggga gagcatcaac cattagtgaa tactttgagg    4260
ttttgaaaca actaaagcca attgtgtccc tttgcatgaa ggttgccccc tccactaagt    4320
tttcctctca agtgtttaga atctattctg aaatgatgag ggtcaatgtt agagtgcctg    4380
```

```
cgaatactga cttgactaga ctggaaccca ttggcatttg ggtttctagt gagccaggac   4440
agggtaaatc attctttaca catatgttga gtacctgtct tctgaagtcc tgcaatttag   4500
aaggaattta taccaacccc acaggttcag aatttatgga tggctatatt gggcaggaca   4560
ttcatatcat agatgatgca gggcaaaata gagaggaaaa agatttggcc ttgttgtgtc   4620
agtgtatttc ttctgtgcct tttactgttc caatggcaga tttgacagag aagggcactt   4680
tttatacaag caaaattgtg attgccacca ccaataaatt tgattttacc tcaatggttt   4740
tgacagatcc agcagccctt gaaaggagat ttccgttcca cttgcgcatt agagctgtag   4800
ccagctattc gcgcaacaac aaactagatg tgggcccgttc aatggcggcc atggcagatg   4860
gttcttgctg ggaatattcc acagatggtg gtagggcttg gaagaccctc tccatggatg   4920
aacttgtgaa acaaatcacg gcagtttaca cacagaggtc agatgccctt atggtttgga   4980
aaaggaagtt gaataccatc aggaacgaaa tgagccctgg atcatccacc ggcaggattt   5040 ttgaacccctt agaggaaaca ctctgtgctt tggaacgtcg ctttggtcaa cttgctgata   5100
gtcttaaaga caactatcat aaaacagctg atgagttgat tgaagctata aagatatga   5160 tggcaccgtc acagagccct tttgcatgct ttgctgaatc ctatcgaccc accattaaat   5220
atactgccag tgataaagtt aaatcatggg ttaaaaatca tatgaataga tggaaagaat   5280
ttgtaatgag aaataaaggc tggtttacac tttttctgt gctctcatca tttctctcga   5340
ttcttactct tgtctatttta cactataaaa aggagaagaa agaggaagag agacaggagc   5400
gggcttacaa ccctcaaact gcaatttcta agaaggggg taagcctaag ctctcattag   5460
tgaaaaccac aaactttgtt aatgaagcac cctatatgca agatcttgaa cattgctttg   5520
cacaaacggc ctacatttct tctccagaaa cccaagatat aatacattgt gctgccttga   5580
gtgaagacac catttttggtt tatggacatt ctcagtttta ttttaaccgc tatgaggacc   5640
tgcggttaca ttttaaaggg gccattttc ccatagaagg gggaaaaatt tctcaagtta   5700
ccgtgaatgg acagcctatg gatttgatac ttgtgaagat agataaactt ccaataacat   5760
ttaaaaatta tacaaaatat tatacaactg aggttggcaa ggaaactctt ttaatttgga   5820
attcagaaaa gggcaggttg gccatgcctg ttcaatgtgt ggctccggct ggtccggtgg   5880
agacaatgga aggaacaatt actcataaga cctattcata taagtggca tcaaaaaaag   5940 gaatgtgtgg gggcctttg gtcactagag tgcatggcac attcaaggtt ctgggaatgc   6000
acattgcagg caatgggcaa gttgcacgag ctgcagcagt tcactttata tccaatggtg   6060
cagctggctt tatggatcaa ggtgttgttg tggccaaaga aaagttacaa aagcccattt   6120
atttgccatc taagacagct ttgaatccca gtcccttgaa tggtgtagtc cccgtgaaaa   6180
tggaaccagc tgtgcttagt cctcatgaca ccaggcttga agtcatcatg cccagcgttg   6240
tgaaaacagc ggcagctaag tatagagtta atattttaa tcctgatttt gagatttggg   6300
agagagtggt ggatgagtta aaatcaaagt ttagaaccaa acttggaatt cataaacatg   6360
tctcttttca gaaagcagtt cagggtttct cctcccttc atctcttgat cttttccacat   6420 cccccaggaca aaagtatgtt gaaagggta tgaagaagag agatcttttg tccactgagc   6480
cattttggat gcatcctcaa ttggaaggtg atgttaaaga tatacttggg gccgtttact   6540
ctggtaaaaa gccccataca ttttttgctg cacattgaa agatgagttg cgcaaaaaag   6600
aaaagattgc gcaaggaaag acccgctgca ttgaagcctg ttcaattgac tatgtgattg   6660
cctacagagt tgtaatgtcc tcactctatg aggcaatcta tcaaactccg gctcaggagt   6720
tgggcctggc agtgggaatg aatccctgga cagattggga tccaatgatc aatgttttgc   6780
```

-continued

```
agccatataa ctatggcctg gattactcat cttatgatgg cagcctttct gaacaactga   6840
tgagatatgg agtggaaata cttgcctact gtcatgaaca accagaggct gtaatgattc   6900
ttcatgaacc tgttataaac tctcaacacc ttgtgatgga tgaaatctgg catgtgaatg   6960
gtggaatgcc ctcaggggcc ccatgtacaa ctgtgctaaa ttccatatgc aatctgctag   7020
tttgtacata tttggcctat gagcagagct tggatattga ggtgttaccc attgtttatg   7080
gagatgatgt aattttttct gtttcatccc ctttggatgc tgaatacttg gttcagagtg   7140
cagcccaaaa ttttggaatg gaagtgacct catcagataa atctggtccc cctaaacttt   7200
tgaaaatgga tgagattgaa tttttaaaga ggacaacaaa atttttttcct ggctccacct   7260 acaaggtggg ggccttgagc ctggatacca tggaacaaca tattatgtgg atgaagaatt   7320
tggaaacctt tccagaacaa cttgttagtt ttgagaatga attggtgttg catgggaaag   7380
aaatttatga tgattataaa aataggttta atcctatttt gaatcaatgg cgagtgtgca   7440
tgcaggacta tgaagtggcc ctgcatcgca tgctacgcta tgtttttgat tgaattgatt   7500
tagtttgatt ttgattttat tagctttagt ttatgtaagt tagaattaga ttattttagt   7560
ttagttttaa agattttgat ttgattgaat ttggcccacc aatc                    7604
```

<210> SEQ ID NO 2
<211> LENGTH: 7609
<212> TYPE: DNA
<213> ORGANISM: Ljungan virus 145SL

<400> SEQUENCE: 2

```
tttgaaaggg gtctcctggt ggggtgggta cgtctctcgc tcattgagtg ggggcgtggc     60
tcaccaacca cacctggttg gtccccaggt tcatgcaata accacttttt gtaatcttta    120
catctaagct taattcaccc actagaactg gacgaaaccg cttggaataa gtttggttct    180
ctcttgagtg tgttttgtgt tagcataatt tctgtctcta gagtgcttta cactctagta    240
ggggctgtac ccgggcggtc ccactcttca caggaatctg cacaggtggc tttcacctct    300
ggacagtgca ttccataccc gctccacaat agaagatgat gtatatcttt gtttgtgaaa    360
tgctcatgaa acgtgtgtgt aggcgtagcg gctacttgaa tgccagcgga accccccctag    420 tggtaacact agcctctggg cccaaaaggc atgtctctga ccattcaagt acacaacccc    480
agtgatacac acatttagta atggctcagt aatggacatt gattgatcat cagacaattg    540
ttaggaggcc taggtatgac gggctgaagg atgccctgga ggtacccgca ggtaacctta    600
agagactgtg gatctgacca ggggcccacc atggaaacat gggtagaagt cttcggacct    660
tgggttaaaa aacgtctagg cccgcccccc acagggatgt ggggtttccc ttataacccc    720
aatatcacat tatggctgca accaagatga atcccgttga gaatcttctt tctactgtct    780
cctccaccgt tggctcactg ctacaaaatc ccaccatgga agaaaaggaa atggactcag    840
atcgtgttgc ggcatccacc actactaacg ctggaaatgt agttcaggct tcagttgccc    900
ccaccatgcc aattaaacca gatttcaaga acacggataa ctttttgtca atgagttata    960
gcccaaatac tgcacctaca aatccaacaa aaatggtaca tttggctaat ggaacatgga   1020
ctacatcgca gcatcgacag tctttggttg catcgattca gctaccacag gcattttggc   1080
ccaatgaacg ctatccggct tggggtcaat cacgctattt tgctgcagtc cgatgtggct   1140
ttcatattca ggttcaattg aatgttaaca ttggctcagc aggttgtttg atagctgcct   1200
atatgcccaa aagtgcacat gatcatatgg atacatatac atttagttcc tacaccaatt   1260
```

```
tgcctcatgt tctgatgaat gctgccacca cgtctcaggc tgatttgtat atacccctatg   1320 tgcataatca taattatgca aagacagatt cagatgactt gggtggtata tacatttggt   1380
gttggtctgc cctcacagtt ccatcaggtt ctccgacaac tgttgatgtc acaattttg    1440 gctccttgct tgacttggac ttccagtgcc ctagaccacc aggtgctaat actgtcatat   1500
ttacacaagg caaagaact  gccaggaaaa ccaaagcaac aaaatttaaa tggacaagga   1560
ataaaataga cattgctgaa ggtcctggcg ctcttaatat tgccaatgtc ttgtctacta   1620 caggggcca  aactgttgcc ctcgttgggg aaagagcttt ctacgatccc agaactgcag   1680
gagccgctgt gcggtgtaag gatttgatgg aaattgccag aatgccatca gtctataagg   1740
gggagagaac tgaacctgga ggaactaatg gctatttttca atggtctcat acgcactccc  1800
ctataaattg ggttttgac  ggggggaattc atttggaaga catgcccaat ctaaatttgt  1860
tttcctcatg ctataactat tggagaggct caattgtttt gaaactcact gtgtatgcat   1920
caacctttaa caagggtaga ttgagaatgg ccttcttccc aaatcatgat gcaaggtaca   1980
cagaggaaga agcacaaaat gccatcttca tggtgtgtga tattgggctc aacaacactt   2040
ttgaaatgac catcccatac acctggggaa actggatgag accaactagg ggatctgtca   2100
ttggatggct taggattgat gttttgaatc gcctcactta taacagttcc tcacccaatg   2160
ctgttaattg cattcttcag gttaaaatgg ggaatgatgc caaatttatg gtacccacca   2220
catctaacat tgtgtgggaa ggtctccact catggggggtc tgagatggac ttactggaca  2280
gtttggataa tccagaagag attcaagata tggaggaacc agaatctgaa atgtgtggagg  2340 ccgcacaagg agaggaagcc gccactgccg ttggccttcg agccaccgaa aatgatggat   2400
ccctatctga acaacaaaac atggcacaac caatgttttt gaattttaag caacatagag   2460
tggacattta ctctgcttcc cacaccaaag ttgaccatat ttttggtagg gcgtgggcag   2520 tgggaattt  taatgtgact aatgctaata tatccaaatt tgaccttaac tttcccacaa   2580
ccacacatgg tgcattgtgt cgcttcttct gtttctggac gggagagctt aacttgcata   2640
ttttgaacat ttcttcttcc aatgctccag tcaaagttgc tcacacatgg tttggcacag   2700
attcaggcat tgccaggact gcaactttgg aatcaaacgg ggttatcatc ataccaccaa   2760
atgagcaaat gacactctgc ataccctatt attctgaggc accattgcgc tgtgttaagg   2820
ggccacattc agctggtgct ggattgggct caattttcac acagtgtatt ggcaacagcg   2880
ttaataacag gattcaaatt tttgttagtt ttcgctgccc aaacttcttt tttcccctttc  2940 ctgcacccca tgaggcttct tcaaggtcaa ttttgcagag aatttccact gctagcgcag   3000
atgagttaga agctgtcttg gacgcaaaaa cacctgatgc tcctgtgcgc ttgtgctacc   3060
aaccagagga tcctttgaga caacttaggg aggcagctaa ggcatatttc aatattatgc   3120
acaatgatga gatggactat tctggaggta aattcttgaa tcagtgtggt gatgtggagt   3180
ccaatccagg tcctgatatt gaattagtct ataagaacag aggcttttat aaacattatg   3240
gggttaggtt tggtggcttt atttaccatc ttaattcaca agacattttg tcgacagcca   3300
tcactggaaa atcagacttc ataaaagagg aagatgatgg taaatggaca catgctatga   3360
ctgcacccct ggattatttt actgagaagt atgtgaaatc aatggttggt tcaaaacaca   3420 ttttttcgc cacatcaaat tgtgaaacca ttgccaggga tttgttttcca ggaaagaagg   3480 agattagtca atctaaagct ttgggtatta ttggtgtgat ccttctttct gcatctcttt   3540
tatccctact tgccgttcca tgggattatt cctcacttca gacagtttat aatcaatcaa   3600
ttgaagggga tgcttcaggc ttaacacttt tgagccagag atgcatgact ttttttttcca  3660
```

-continued

```
ataccatgtg tgaaactttt aataatgatc ttgtgaagtt tataattaag attttagtta    3720
ggcttctttg ctatattgtt ctttattgtc atgcccctaa tatgcttaca acaatgtgtt    3780
taggcaccct tttggttttg gatattacca catgtgagat tttatcagcc aatacaaagg    3840
ccctgtttca agctcttctt gatggagacg tcaagaattt ggtttggaag attgcagaga    3900
acatgcagtt tgcccagtct acagatgagc aggcagagga aatggctgcc accttttcat    3960
ttgccaaaga catggttgac attcatccaa ttggggctga gccatttcaa aaccaaggct    4020
ttagggagtt taatgatgtg tcaatgtcct ttcgccacat tgaatggtgg cttacaatgt    4080
ttaagaaagt ttacaatgtt cttaagggca ttttctctcc atccattgag cagaaagcgg    4140
tggcgtggtt ggatcgcaac caagaatatg ttgcatcaat cttagatcat tgctctgaca    4200
tgattatccg catgaaagac ccaaaacaac agcggaaccc caagaccatt gaagaatatt    4260
ttgatgtgtt aaagaaaatg aagcccttgg tgtcactctg cattaaagtt gccccgtcaa    4320
caaagttttc atcccaagtg tttaggttgt attcagagct aatgaaggtt aatgttagag    4380
tgccggttaa cacagatctc acacgcattg agccaattgg tgtgtggatc tccagtgagc    4440
caggtcaggg aaaatctttc tttactcaca tgcttagcac ttcacttttg aaaagttgta    4500
atttggatgg ggtgtatacc aatgccacag gctctgagtt tatggatgga tatgttggtc    4560
aagatataca cattattgat gatgcaggac aaaatcggga agagaaggat tggctctgc     4620
tgtgccagtg catctcatct gtgccattta ctgtacctat ggctgatcta acagagaaag    4680
ggacatttta taccagcaag attgttattg ccacaaccaa caagagtgat ttcaattgca    4740
tggttttgac agatccagct gctctagaga ggcgtttccc atttaatttg agaattaggg    4800
cagttaaaag ttttatgaat aaggacagaa agttggatgt gccaagatca atgggagcca    4860
tggcagatgg atcctgctgg gagtgctcta tggactatgg cagaacctgg aacaccgtgg    4920
tgatgagaga tcttgtgaaa caaataacag aaatgtataa acaaagagat gatgccctga    4980
ctgtttggaa gtataagtta aatcagatta ggaatgagat gtcccctggt gactcaattg    5040
gccgcattct cgatccaatg gaggagacac tctgttcatt ggagcgcagg tttggccagt    5100
tggcagatag tcttagagaa aattaccata ggacagctga tgaactaatt gaagttatag    5160
aagacatgat ggcaccaggg aatagtccct ttgcatgctt cgaaagtgta gcaccatcac    5220
ttaaaccaag aacagcttgt caaaaagtta agattgggt aaaacaacac atgattagat    5280
ggggcaactt tgtgatgagg aataaaggct ggtttacact ttttctgta ctttcatctt     5340
ttctttcaat tcttactctt gtttatttac attataaaaa agagaaaaaa gaggaagaaa    5400
gacaagagcg ggcttacaac cctcaaactg caactcccaa gaaggggggt aagccaaagc    5460
tctctttggt aaaaactaca aattttataa atgaggcacc atatatgcag gatttggaac    5520
actgctttgc ccaaacagcc tacatttcat ccccagagac tcaggatata attcattgtg    5580
ctgccttgtg tgaggatacc attttggttt atggacattc acaatttat tttaaccgct     5640
atgaagattt gcggttacat tttaaaggag ccattttcc tattgagggt ggaaaaattt     5700
cacaagttac tgtgaatggg cagccgatgg atttgattct tgttaaaata gacaaacttc    5760
ccataacctt taaaaattat accaaatatt acacaactga aattgggaag gaaactcttt    5820
taatttggaa ttctgagaaa gggagactgg ctatgccagt ccaatgtgtt gccccggctg    5880
gaccggtgga acaatggaa ggcaccatca ctcataaaac ctattcctac aaagtggcat     5940
caaagaaagg catgtgcggt ggactcctag ttactagagt gaatgaaaca tttaaggttt    6000
```

-continued

| | |
|---|---:|
| tggggatgca cattgctggg aacggacagg ttgcgcgggc cgcagcagtt cacttcattt | 6060 |
| caaatggggc tagtggtttt atggatcagg gggttgtggt tgcaaaagag aagatgcaga | 6120 |
| aaccaatttta tttgccatct aaaacagcac taaatcctag ccctttgaat ggtgttgtgc | 6180 |
| ccgtgaagat ggagcctgca gttcttagcc ctcatgatgt tagacttgaa gtgattatgc | 6240 |
| caagcgtggt taaaaatgca gcagccaagt acagagttaa catcttcaac ccagattttg | 6300 |
| aaatctggga gagggtggtt gatgaattga agcaaggtt tcgatctaag cttggcatac | 6360 |
| acaaacatgt ttctcttcaa aaggctgtgc aaggttttc ctcccttcg tctcttgatc | 6420 |
| tttctacctc tccagggcaa aagtatgttg aaaaggaat gaagaaaagg gatcttttgt | 6480 |
| ccactgaacc attttggatg catcctcaat tggaaagtga tgttaaagat atacttgggg | 6540 |
| cagtttattc tggtaagaaa ccccacacat tttttgctgc ccacttgaaa gatgagttgc | 6600 |
| gcaagaagga aaagattgcg caaggaaaga cccgctgcat tgaagcatgt tcaattgatt | 6660 |
| atgttattgc ctatagagtt gtgatgtcct ctctctatga ggcaatttat caaaccccag | 6720 |
| ctcaagaatt gggcttggca gtgggaatga atccctggac agattgggat ccaatgatta | 6780 |
| atgttttgca gccttataat tatgttttag attattcatc ctatgatggc agtctttctg | 6840 |
| aacagttaat gagatatggt gttgaaatac ttgcttattg tcatgagcaa ccagaagctg | 6900 |
| tgatgattct ccatgagcca gttataaatt cgcaacacct tgtgatggat gaaatctggc | 6960 |
| atgtaaatgg aggaatgccc tcaggagccc catgtacaac tgtgctaaac tctatatgta | 7020 |
| atttgctggt ttgtacatat ttggcttatg agcagagttt ggacattgag gtgttgccta | 7080 |
| ttgtttatgg ggatgatgtg atttttttctg tttcttcacc attggatgct gaatatttgg | 7140 |
| ttcagagcgc tgcccaaaat tttggaatgg aagtgacatc atcagataaa tctggccccc | 7200 |
| caaaactttt gaaaatggat gagattgaat ttttaaagag gacaacaaaa tttttcccg | 7260 |
| gctccaccta aaggtggggg ccttgagcc tggataccat ggaacaacac attatgtgga | 7320 |
| tgaagaatct ggaaaccttt ccagaacaac ttgttagctt tgaaaatgag ttggtgttgc | 7380 |
| atgggaaaga aatttatgat gattataaaa ataggtttaa tcctatttg aatcaatggc | 7440 |
| gagtgtgcat gcaggactat gaagtggctc tgcatcgcat gctacgctat gtttttgatt | 7500 |
| agattgattt agtttgattt tgattttatt agttttattt taggttagaa ttagattatt | 7560 |
| ttagtttagt tttaaggatt ttgatttgat tgaatttggc ccaccaatc | 7609 |

<210> SEQ ID NO 3
<211> LENGTH: 7608
<212> TYPE: DNA
<213> ORGANISM: Ljungan virus 174FL

<400> SEQUENCE: 3

| | |
|---|---:|
| tttgaaaggg gtctcctggt ggggtgggta cactcctcgc tcaatgagtg ggggtgtggc | 60 |
| tcattgccca cacctggttg gttcccaggt tcatacaata accatcaata aacttctcaa | 120 |
| catctaagct actactatcc cacactaaac tggacgaagc cgcttggaat aagtctagtt | 180 |
| tcattctgtg tgtgttttgc actgaaatta tttctgtctc tggggtgctt tacacttcag | 240 |
| taggggctgt acccgggcgg tcccactctt cacaggaatc tgcacaggtg ctttcacct | 300 |
| ctggacagtg cattccacac ccgctccaca gtagaagatg atgtgtgtct ttgcttgtga | 360 |
| aaagcttgtg aaaatcgtgt gtaggcgtag cggctacttg agtgccagcg gactacccct | 420 |
| agtggtaaca ctagcctctg ggcccaaaag gcatgtcaat tgaccactca ggtacacaac | 480 |
| cccagtgatg cacacgtcta gtaacggctt agtaacgagc attgattgat catttgaaaa | 540 |

-continued

```
ctgctaggag gtttaggtat gacgggctga aggatgccct gaaggtaccc ataggtaacc      600
ttaagcgact atggatctga tcagggcccc accatgtact acatgggtag aagtcttcgg      660
accttgggtt aaaaaacgtc taggcccgcc ccccacaggg atgtgggggtt tcccttataa     720 ccccaatatt gtataatggc tgcatccaaa atgaatcccg ttggcaacct gctttccaca     780
gtctcctcaa ccgttggatc tcttctacaa aaccccctctg ttgaagaaaa ggaaatggat    840
tctgaccgtg ttgctgcctc caccacgacc aatgctggta atttggtgca agcttctgtg    900
gctccaacca tgcctgtaaa accagacttt aagaacacag atgacttctt gtccatgagc    960
taccgctcaa caacggcccc aaccaacccg acaaaaatgg ttcacttagc gcatggaact   1020
tggacaacta atcagcacag acaggcattg gttgcatcaa ttaccctacc acaggcattc   1080
tggcccaatc aagattttcc agcatggggg caatctcgct attttgcagc agtgcgctgt   1140
ggctttcata taacaagtgca gttgaatgtt aacattggtt ctgccggctg cttgattgcc   1200
gcatacatgc aaagacggc ccatgatcat atgggtacct atactttttgg ctcctacacc   1260 aacctgccac atgttttgat gaatgcagca acgacatctc aggctgatct ctatatacccc  1320 tatgttttta atcacaatta tgcacgaact gattcagatg acttaggagg tatttacatt    1380
tgggtatggt cagctctcac agttccatca ggttccaccta ctacagtgga tgtcaccatt   1440
tttggttcat tactcgactt agattttcaa tgtcctcgtc ccctggagc agccacagta    1500 atctacacac aagggaaaag aactgttcga aagaccaaaa catcaaagtt taaatgggtc    1560
aggaataaaa ttgacatagc tgaaggccca ggagcaatga acattgctaa tgttctctcc    1620
acaactggcg tcaaactat tgccttggtt ggtgaaagag cattctatga cccaagaaca    1680
gctggtgctg cagtaaggtg caaagatctc atggagatcg ccagaatgcc gagtgtgttc    1740
ttgggagaga gcactgaacc agatggtcga agaggctatt ttacctggtc acatacaatc    1800
tcacctgtta ttgggtcttt tgatgatcat atttatttag aaaatatgcc caatttgaga    1860
ttgttttcct cttgttataa ttattggaga gggtcttttg ttattaaatt aacagtctat    1920
gcatcaactt tcaacaaagg acgcttgagg atggcattct tcccaaacag agagggcgcc    1980
tacacacagg atgaagccca gaatgcaatc tttgttgtct gtgatatagg cctgaataac    2040
acttttgaga tgaccatccc ctacacttgg ggcaattgga tgaggccaac aagagggaat    2100
tccttgggac atttgaggat tgatgtgctg aatcgtctca catacaacag ttcctccccg    2160
aatgcagtca actgcattct tcagatcaag atgggagatg atgcaatgtt tatggtgccc    2220
accacatcta atctagtttg gcaaggccta cattcctggg gttcagaaat ggacctggtg    2280
gactcccttg acaatccaga agagatacag gataatgagg aaatacaaac tcagaatgtg    2340
gaggcagcac aaggggaaga agctgcaaca gaagttggac ttagggctac agaaaatgat    2400
ggtagtcttt cagaacaact gaatatgagt caacccatgt tcttgaattt caagaagcat    2460
aaagttaaca tctatgcagc atctcacact aaagttgatc atattttttgg cagagcttgg   2520 gcagtaggag ttttttaatac agaaacagct gccatacaaa aatttgattt gcattttcca    2580
acttctaccc atggtgcatt atctagattt ttctgttttt ggactggaga actgaacatt   2640
cacatcttga atgtgtcaac cacaaatgca ttccttgaaag ttgctcacac atggtttggc   2700
actgattctg gaattgctcg gacagccact ttggaatcaa atggaacaat gattatacca    2760
ccaaatgagc aaatgacact ctgtgtgccc tattattctg aggtcccatt aagatgtgtt    2820
aagggctcag acaggaattc agccggtctt ggttctcttt tcacacaagc tgtaggcaga    2880
```

```
acaatttcca atcgggttca aattttTgtg agcttccgct gtcctaattt tttcttccca    2940
ctacccgcgc ccagagaagc cacgtcccga agcatattgg aacgagtgga tgaagcgaat    3000
gcagaagaac ttgaagctgt tttggaagct agaacaccag atgcgccgct ccgcctcaaa    3060
tttaatccag aagacccctt gaaacaattg cgggaagcgg ctaaggccta ctttaatata    3120
atgcacagtg atgaaatgga ttttgccggg gggaaatttt tgaatcaatg tggtgatgtg    3180
gaaactaacc caggccctga cattgagttg gtctataaaa acagaggctt ttataaacat    3240
tatggggtta gatttggtgg ctatatctac catttgaatt cacaggatat tctgtcaact    3300
gcaattacag gcaagtctga tttcattaag gaggaagatg atggcaaatg ggttcatgct    3360
atgacggcac cactggatta ttttactgaa aagtacatca attcaatggt tggttccaaa    3420 catattttt ccgccacctc caattgtgag accattgcca gagaccTttt cccagggaga    3480
aaggaaataa ctcagtccaa agccttggga attattgggg tcattttgtt gtcagcctct    3540
cttctttcct tgcttgctgt accctgggat tattcctcac ttcaaactgt ttataaccaa    3600
tccattgaag gtgacgcttc tggcctcaca cttttaagtc aaagatgcat gactttttt    3660 tctaacacaa tgtgtgaaac ctttaataat gatcttgtta agtttattat taagattttg    3720
gtgcggcttt tgtgctacat cgttctctat tgccatgcac caaatatgct gacaactatg    3780
tgtctgggaa ctcttcttgt tttggacatt acaacttgtg aaatcttgtc tgccaacacc    3840
aaagcactct ttcaggcatt ggtcgatggt gatgtgaaga gtcttgtctg gaaaattgct    3900
gaaaacatgc agtttgccca atccaaagat gaacaagcag aggaaatggc ggcaaccttc    3960
aactttgctt ctgatatggt taattttgtg ccaatggaac agatgagaca agaaggctgg    4020
agagaattta atgatgtttc tatgtccttc cggcatgtag aatggtggct gaccatgttt    4080
aaaaaagtgt ataatggtct gaaaagtatt tttgcaccta gtattgaaca aaggctgtt    4140 gattggatag atcgcaatca agaatatatt gccgatgttt tggaccatgc ttccaacatc    4200
attataaaaa tgaaggaccc aaaagaacag cggaaagcat taaccattag tgaatacttt    4260
gaagttttga agcaattaaa gccaattgtg tctctttgca tgaaggttgc tccctccact    4320
aagttttcct ctcaagtgtt tagaatttat tctgaaatga tgaaggttaa tgttagagtg    4380
cctgcaaata ctgacttgac cagattggaa cccattggca tttgggtttc tagtgagcca    4440
ggacagggta atcatttttt tacacacatg ttgagcacct gccttttaaa atcctgcaat    4500
ttagagggaa tttataccaa ccccactggg tcagaattta tggatggtta tattggacag    4560
gacatccata ttatagatga tgcagggcaa aacagggagg aaaaagattt agccttgttg    4620
tgccagtgta tttcctctgt gccttttacc gtcccaatgg cagatttgac agagaagggc    4680
acttttTaca caagtaaaat tgtgattgct accaccaata aatttgattt tacatcaatg    4740
gttttgacag atccagcagc tcttgaaagg aggttcccgt ttcatttgcg cattagagct    4800
gtagccagct actcgcgcaa taataaatta gatgtggccc gctcaatggc agccatggct    4860
gatggctctt gctgggaata ctctacagat ggtggtaggg cttggaagac tctgtccatg    4920
gatgaacttg tgaaacagat tacggcagtc tatacacaga gatcagatgc ccttatggtt    4980
tggaaaagga agttaaacac cattaggaat gaaatgagtc ctggatcctc caccggtagg    5040
atctttgaac ccttggagga aacacttTgt gctctggaac gccgctttgg tcaacttgct    5100
gatagcctta agacaattac ccacaaaaca gctgatgagc tgattgaggc tatagaagat    5160 atgatgcac catcacagag cccttttgca tgctttgcag aatccTatcg gcccaccatt    5220
aaatacactg ccagtgataa agttaaatcc tgggtcaaaa atcatatgaa tagatggaaa    5280
```

```
gagtttgtaa tgagaaataa aggctggttt acactttttt ctgtgctttc atctttctt    5340
tcaattctta ctcttgttta cttgcattat aaaaaggaaa agaaagagga agagagacaa   5400
gagcgagctt acaaccctca aaccgcaact tttaagaagg ggggtaagcc caagctctca   5460
ttggtgaaaa atacaaattt tgttaatgaa gcaccctata tgcaagatct tgaacactgt   5520
tttgcacaaa cagcctacat ctcatcttca gagacccagg atataataca ttgtgctgct   5580
ttgagtgaag acaccatctt ggtttatgga cactcccagt tttattttaa ccgctatgaa   5640
gatctgcggt tgcattttaa aggggccatt tttcctatag aaggggggaa aatctctcaa   5700
gttactgtga atgggcagcc catggattta attcttgtga aaatagataa acttccaata   5760
acatttaaaa attatacaaa gtactataca actgaggttg gtaaggaaac actcttaatt   5820
tggaattcag agaaaggcag attggctatg cctgttcaat gtgtagcccc ggctggtccg   5880
gtggaaacaa tggaaggaac agtcacccac aagacctatt catacaaggt ggcatcaaaa   5940
aaaggaatgt gtgggggtct cttggttact agagtgcacg gcacatttaa ggttttagga   6000
atgcacattg ctggcaatgg acaagttgca cgagccgcag cagtccactt tatatccaat   6060
ggggctgctg gctttatgga tcagggtgtt gttgtggcca aggaaaaatt gcagaagccc   6120
atttatttgc catccaagac agccttgaat cctagtccct tgaatggagt agttcctgtg   6180
aaaatggagc cagctgtgct tagtcctcat gataccaggc ttgaagttgc catgcccagt   6240
gttgtgaaaa cagcagcagc caagtataga gttaacattt tcaaccctga ctttgagatt   6300
tgggagagag ttgtggatga gctaaagtca aggtttagat ttaaacttgg gattcataaa   6360
catgtttctt tccaaaaagc agttcagggt ttttcttctc tttcatctct tgatctttcc   6420
acttctccag gacaaaagta tgttgaaaaa ggcatgaaga agagagatct tttatccact   6480
gaaccatttt ggatacatcc tcaattggaa aatgatgtta agatatact tggggctgtt   6540
tattctggca aaaaaccca tacatttttt gctgcccatt tgaaagatga attgcgcaaa   6600
aaagaaaaga ttgcacaagg caagacccgc tgcattgaag cctgctcaat tgactatgtg   6660
attgcctata gagttgtaat gtcctctctc tatgaggcaa tctatcaaac cccagctcag   6720
gaattaggct tggcagtggg gatgaatccc tggacagact gggatccaat gattaatgtt   6780
ttgcaaccat ataattatgg tttggattat tcatcttatg atggcagtct ttctgagcag   6840
ctgatgaggt atggtgtgga aatacttgcc tattgtcatg aacaaccaga ggctgtgatg   6900
attcttcatg aaccagttat aaactcacaa caccttgtga tggatgaaat ttggcatgta   6960
aatggaggaa tgccctcagg agccccatgt acaactgtgc taaattcyat atgcaatctg   7020
ctggtttgta catatttggc ttatgagcaa agttttggata ttgaggtgtt gcccattgtt   7080
tatggagatg atgtgatttt ttccgtttcc tcccctttgg atgctgaata tctggttcag   7140
agtgcagcca gaaattttgg gatggaagtg acctcatcag ataaatctgg tcccccaaga   7200
cttttgaaaa tggatgagat tgaatttta aagaggacaa caaatttttt tcctggctcc   7260
acctataagg tgggggcctt gagcctggat accatggaac aacatattat gtggatgaag   7320
aatttggaaa cctttccaga caacttgtt agctttgaaa atgagttggt gttgcatggg   7380
aaagaaattt atgatgatta taaaagtagg tttaatccta ttttgaatca atggcgagtg   7440
tgcatgcagg actatgaagt ggccctgcat cgcatgctac gctatgtttt tgattaaatt   7500
gatttaattt gatttgatt ttgttagttt tagtttaagt aagttagaat tagattattt   7560
taatttagct ttaaagattt tgatttgatt gaatttggcc caccaatc               7608
```

```
<210> SEQ ID NO 4
<211> LENGTH: 60
<212> TYPE: PRT
<213> ORGANISM: Ljungan virus

<400> SEQUENCE: 4

Gln Ser Arg Tyr Phe Ala Val Arg Cys Gly Phe His Ile Gln Val
 1               5                  10                  15

Gln Leu Asn Val Asn Ile Gly Ser Ala Gly Cys Leu Ile Ala Ala Tyr
            20                  25                  30

Met Pro Lys Thr Ala His Asp His Met Asn Thr Tyr Thr Phe Gly Ser
        35                  40                  45

Tyr Thr Asn Leu Pro His Val Leu Met Asn Ala Ala
    50                  55                  60

<210> SEQ ID NO 5
<211> LENGTH: 60
<212> TYPE: PRT
<213> ORGANISM: Ljungan virus

<400> SEQUENCE: 5

Ser Phe Arg Cys Pro Asn Phe Phe Pro Leu Pro Ala Pro Arg Glu
 1               5                  10                  15

Ala Thr Ser Arg Ser Ile Leu Glu Arg Val Asp Glu Ala Asn Ala Glu
            20                  25                  30

Glu Leu Glu Ala Val Leu Glu Ala Arg Thr Pro Asp Ala Pro Leu Arg
        35                  40                  45

Leu Lys Phe Asn Pro Glu Asp Pro Leu Lys Gln Leu
    50                  55                  60

<210> SEQ ID NO 6
<211> LENGTH: 60
<212> TYPE: PRT
<213> ORGANISM: Ljungan virus

<400> SEQUENCE: 6

Pro Met Glu Gln Met Arg Gln Glu Gly Trp Arg Glu Phe Asn Asp Val
 1               5                  10                  15

Ser Met Ser Phe Arg His Val Glu Trp Trp Leu Thr Met Phe Lys Lys
            20                  25                  30

Val Tyr Asn Val Leu Lys Ser Ile Phe Ala Pro Ser Ile Glu Gln Lys
        35                  40                  45

Ala Val Asp Trp Ile Asp Arg Asn Gln Glu Tyr Ile
    50                  55                  60

<210> SEQ ID NO 7
<211> LENGTH: 60
<212> TYPE: PRT
<213> ORGANISM: Ljungan virus

<400> SEQUENCE: 7

Thr Gly Ser Glu Phe Met Asp Gly Tyr Ile Gly Gln Asp Ile His Ile
 1               5                  10                  15

Ile Asp Asp Ala Gly Gln Asn Arg Glu Glu Lys Asp Leu Ala Leu Leu
            20                  25                  30

Cys Gln Cys Ile Ser Ser Val Pro Phe Thr Val Pro Met Ala Asp Leu
        35                  40                  45

Thr Glu Lys Gly Thr Phe Tyr Thr Ser Lys Ile Val
    50                  55                  60
```

-continued

```
<210> SEQ ID NO 8
<211> LENGTH: 10
<212> TYPE: PRT
<213> ORGANISM: Homo sapiens

<400> SEQUENCE: 8

Ala Leu Gln Cys Gly Arg His Val Asp Val
  1               5                  10

<210> SEQ ID NO 9
<211> LENGTH: 9
<212> TYPE: PRT
<213> ORGANISM: Homo sapiens

<400> SEQUENCE: 9

Ala Ala Val Leu Pro Gln Thr Ala His
  1               5

<210> SEQ ID NO 10
<211> LENGTH: 12
<212> TYPE: PRT
<213> ORGANISM: Homo sapiens

<400> SEQUENCE: 10

Ala Val Ala Glu Glu Val Asn Ala Ile Leu Lys Ala
  1               5                  10

<210> SEQ ID NO 11
<211> LENGTH: 4
<212> TYPE: PRT
<213> ORGANISM: Homo sapiens

<400> SEQUENCE: 11

Ile Phe Ser Pro
  1

<210> SEQ ID NO 12
<211> LENGTH: 9
<212> TYPE: PRT
<213> ORGANISM: Homo sapiens

<400> SEQUENCE: 12

Glu Arg Gly Phe Phe Tyr Thr Pro Lys
  1               5
```